(12) United States Patent
Kim et al.

(10) Patent No.: US 11,229,503 B2
(45) Date of Patent: Jan. 25, 2022

(54) IMPLANT SURGERY GUIDING METHOD

(71) Applicants: Do Hyun Kim, Seoul (KR); Yu Jin Kim, Seoul (KR)

(72) Inventors: Do Hyun Kim, Seoul (KR); Yu Jin Kim, Seoul (KR)

(*) Notice: Subject to any disclaimer, the term of this patent is extended or adjusted under 35 U.S.C. 154(b) by 117 days.

(21) Appl. No.: 16/483,587

(22) PCT Filed: Feb. 3, 2017

(86) PCT No.: PCT/KR2017/001236
§ 371 (c)(1),
(2) Date: Aug. 5, 2019

(87) PCT Pub. No.: WO2018/143497
PCT Pub. Date: Aug. 9, 2018

(65) Prior Publication Data
US 2019/0380811 A1 Dec. 19, 2019

(51) Int. Cl.
*A61C 8/00* (2006.01)
*A61C 1/08* (2006.01)
(Continued)

(52) U.S. Cl.
CPC ............. *A61C 1/084* (2013.01); *A61B 34/20* (2016.02); *A61C 8/009* (2013.01);
(Continued)

(58) Field of Classification Search
CPC ........... A61C 1/084; A61C 8/009; A61C 3/00; A61C 8/0001; A61C 13/34; A61B 34/20; A61B 2034/2055
See application file for complete search history.

(56) References Cited

U.S. PATENT DOCUMENTS 7,457,443 B2   11/2008   Persky
2013/0108979 A1   5/2013   Daon
(Continued)

FOREIGN PATENT DOCUMENTS

JP   2013-034764 A   2/2013
KR   10-2013-0123192 A   11/2013
(Continued)

OTHER PUBLICATIONS

KR-20130123192-A Description English Translation (Year: 2013).*
KR-20160106991-A Description English Translation (Year: 2016).*

*Primary Examiner* — Ralph A Lewis
(74) *Attorney, Agent, or Firm* — IP Legal Services, LLC

(57) ABSTRACT

The present disclosure provides an implant surgery guiding method of guiding a position, direction and depth of a fixture to a dentist by real-time images. The implant surgery guiding method includes: (a) generating a 3D oral cavity image for a patient; (b) designing a target placement including a target position and a target orientation of a fixture based in the 3D oral cavity image; (c) attaching an oral marker comprising a first pattern to a jawbone or a surrounding body portion of the patient, determining a spatial relationship between the oral marker and the jawbone, attaching a handpiece marker comprising a second pattern on a handpiece of a dentist, and determining a spatial relationship between the handpiece marker and the handpiece; and (d) estimating positions and orientations of the jawbone and the handpiece based on changes in positions and orientations of the oral marker and the handpiece marker while tracking the motions of the oral marker and the handpiece marker, and displaying a jawbone image portion and a handpiece image portion on a screen reflecting real-time changes in the positions and orientations of the jawbone and the handpiece.

14 Claims, 31 Drawing Sheets

(51) Int. Cl.
  *A61B 34/20* (2016.01)
  *A61C 3/00* (2006.01)
  *A61C 13/34* (2006.01)
(52) U.S. Cl.
  CPC ......... *A61B 2034/2055* (2016.02); *A61C 3/00* (2013.01); *A61C 8/0001* (2013.01); *A61C 13/34* (2013.01)

(56) References Cited

U.S. PATENT DOCUMENTS

| | | |
|---|---|---|
| 2013/0131504 A1 | 5/2013 | Daon |
| 2013/0131505 A1 | 5/2013 | Daon et al. |
| 2014/0126767 A1 | 5/2014 | Daon et al. |
| 2014/0228675 A1 | 8/2014 | Daon |
| 2014/0276955 A1 | 9/2014 | Daon et al. |
| 2015/0119685 A1 | 4/2015 | Daon et al. |
| 2015/0132720 A1 | 5/2015 | Daon |
| 2015/0147714 A1 | 5/2015 | Daon |
| 2015/0150641 A1 | 6/2015 | Daon et al. |
| 2015/0182296 A1 | 7/2015 | Daon |
| 2016/0045279 A1 | 2/2016 | Daon et al. |
| 2016/0074127 A1* | 3/2016 | Merritt .................... G06T 7/593 433/29 |
| 2016/0078627 A1 | 3/2016 | Daon et al. |
| 2016/0135904 A1 | 5/2016 | Daon et al. |
| 2016/0166174 A1 | 6/2016 | Daon et al. |
| 2016/0220316 A1 | 8/2016 | Daon et al. |
| 2016/0287336 A1 | 10/2016 | Kim et al. |
| 2016/0345917 A1 | 12/2016 | Daon et al. |
| 2016/0367321 A1* | 12/2016 | Daon ..................... A61C 1/082 |
| 2017/0143431 A1 | 5/2017 | Daon |
| 2018/0004802 A1 | 1/2018 | Daon |
| 2018/0055579 A1 | 3/2018 | Daon et al. |

FOREIGN PATENT DOCUMENTS

| | | | |
|---|---|---|---|
| KR | 20130123192 A | * | 11/2013 |
| KR | 10-2014-0130582 A | | 11/2014 |
| KR | 10-1491704 B1 | | 2/2015 |
| KR | 10-1544773 B1 | | 8/2015 |
| KR | 10-2016-0106991 A | | 9/2016 |
| KR | 20160106991 A | * | 9/2016 |
| KR | 10-2017-0091847 A | | 8/2017 |
| WO | 2016/139149 A1 | | 9/2016 |

\* cited by examiner

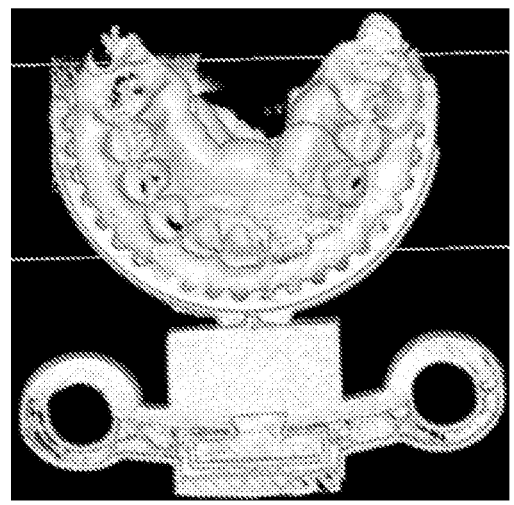
FIG. 11
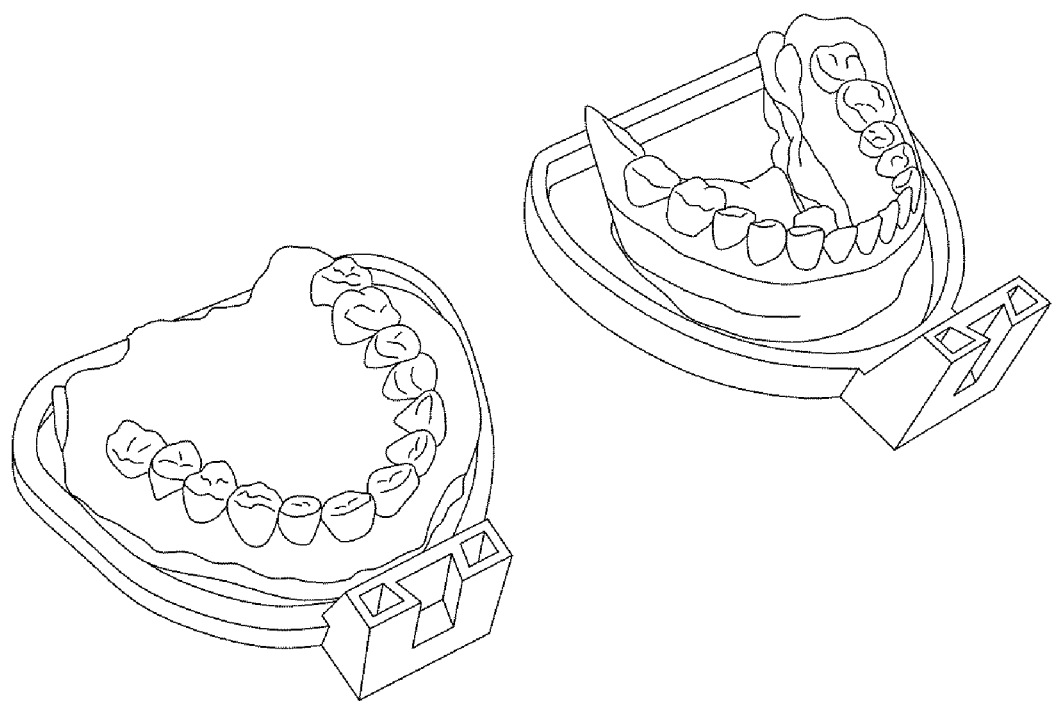

FIG. 33
[During marker registration]
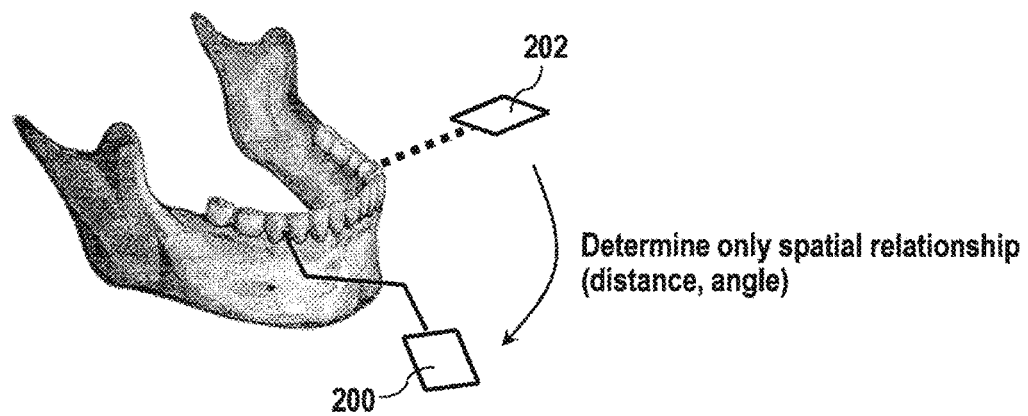
Determine only spatial relationship (distance, angle)
[During jawbone tracking]
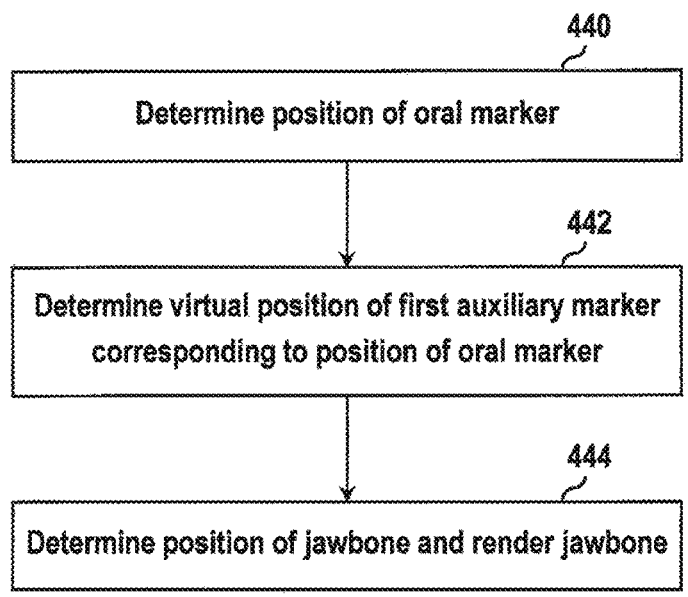

FIG. 34
[During marker registration]
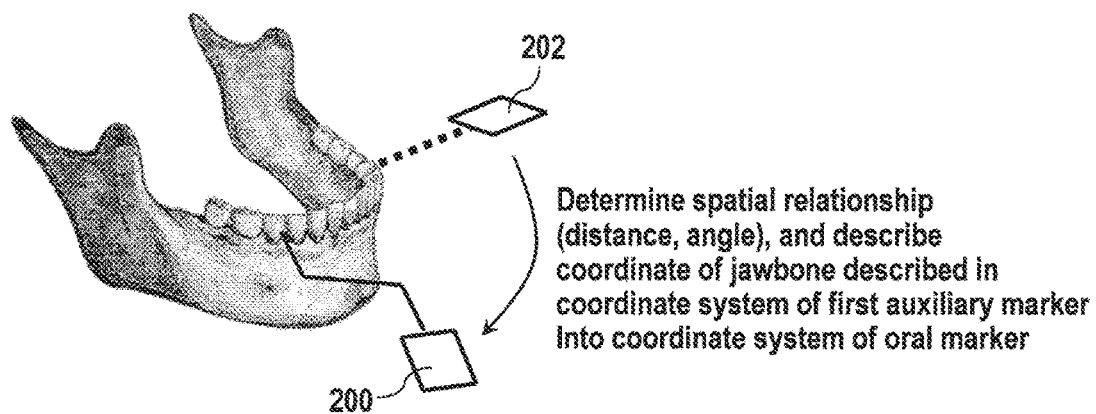
Determine spatial relationship (distance, angle), and describe coordinate of jawbone described in coordinate system of first auxiliary marker into coordinate system of oral marker
[During jawbone tracking]
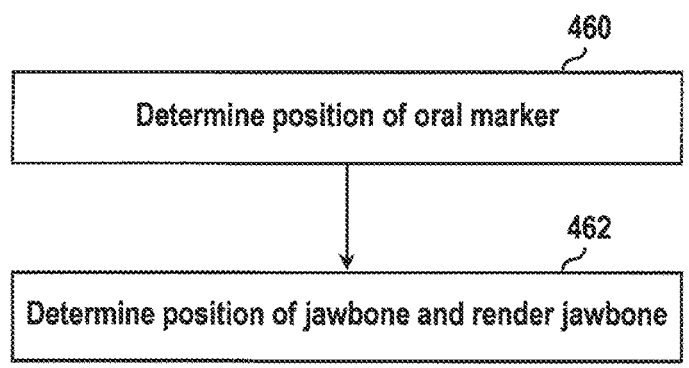

IMPLANT SURGERY GUIDING METHOD

CROSS REFERENCE TO RELATED APPLICATIONS

This application is a National Stage Patent Application of PCT International Patent Application No. PCT/KR2017/001236 (filed on Feb. 3, 2017) under 35 U.S.C. § 371, the teaching of which is incorporated herein in its entirety by reference.

TECHNICAL FIELD

The present disclosure relates to a method of generating and displaying medical images and, more particularly, to a method of generating and displaying images for supporting treatment in a dentistry.

BACKGROUND ART

In an implant procedure which is a kind of a dental prosthetic treatment, an implant fixture (hereinbelow, abbreviated as "fixture") which is an anchoring post made of a metal such as titanium is placed in an alveolar bone, an implant abutment (hereinbelow, abbreviated as "abutment") is fastened to the fixture by an abutment screw after the fixture is fused with a bone tissue, and then an artificial tooth/teeth such as a crown or a bridge is placed on the abutment. The abutment connects the artificial tooth/teeth to the fixture and transfers a force applied to the artificial tooth/teeth to a jaw through the fixture.

In the implant prosthetic treatment, a high level expertise is required for accurately implanting the fixture by properly determining a fixture placement position and drilling to a required depth in a correct direction. If the position, orientation, or depth of the fixture is slightly wrong, the error can be compensated by making and using a customized abutment adapted to the patient. If the error is significant, however, an aesthetics and functionality of the implant prosthesis may be remarkably deteriorated.

Accordingly, the implant treatment is performed by only experienced dentists, which is one of obstacles to lowering a cost of the treatment. On the other hand, even the experienced dentists can make mistakes and may need a way to check whether the procedure is being performed correctly, but there is no such a checking and/or verification method yet.

DISCLOSURE OF INVENTION

Technical Problem

To solve the problems above, provided is an implant surgery guiding method of guiding a position, direction and depth of a fixture to a dentist to significantly reduce a possibility for errors and allow the dentist to assure that the procedure is being performed correctly.

Technical Solution

According to an aspect of an exemplary embodiment, an implant surgery guiding method includes: (a) generating a 3D oral cavity image of a patient; (b) designing a target placement including a target position and a target orientation of a fixture based in the 3D oral cavity image; (c) attaching an oral marker comprising a first pattern to a jawbone or a surrounding body portion of the patient, determining a spatial relationship between the oral marker and the jawbone, attaching a handpiece marker comprising a second pattern on a handpiece of a dentist, and determining a spatial relationship between the handpiece marker and the handpiece; and (d) estimating positions and orientations of the jawbone and the handpiece based on changes in positions and orientations of the oral marker and the handpiece marker while tracking the motions of the oral marker and the handpiece marker, and displaying a jawbone image portion and a handpiece image portion on a screen reflecting real-time changes in the positions and orientations of the jawbone and the handpiece.

The operation (a) may include: acquiring at least one base image of an oral cavity including the jawbone of the patient; preparing an oral gypsum model of the patient and acquiring a gypsum model image of the oral gypsum model; and combining the at least one base image and the gypsum model image to generate the 3D oral cavity image.

The operation (a) may include: applying an impression material to an impression assistant tool which may be partially exposed out of an oral cavity, taking an impression by making the patient to bite the impression material, and acquiring a first base image while the impression is being taken; acquiring a second base image of the impression assistant tool to which the impression cured and separated from the oral cavity is attached; and preparing an oral gypsum model of the patient and acquiring a third base image of the oral gypsum model. Here, the operation (a) may further include: combining the first through the third base images to generate the 3D oral cavity image.

In case that at least one of the first through the third base images is a CT image, it is preferable to convert the CT image among the first through the third base images into a vector image to determine a first through a third vector images from the first through the third base images; and combine the first through the third vector images to generate the 3D oral cavity image.

When the first through the third vector images are combined to generate the 3D oral cavity image, the first and the second vector images may be combined using respective portion corresponding to the impression assistant tool in the first and second vector images, and the second and the third vector images may be combined using surface shape information in teeth portion.

When the first through the third base images are combined to generate the 3D oral cavity image, It is preferable to convert vertices for of the impression portion such that a negative imprint portion for teeth in the second vector image is converted into a positive imprint portion; and combine the positive imprint portion for teeth in the second vector image with the corresponding teeth portion in the third vector image.

In designing the target placement, teeth elements according to a predetermined standard teeth model may be disposed in the 3D oral cavity image, a teeth arrangement may be adjusted, and then a standard tooth conforming to the standard teeth model may be disposed at a tooth missing location where a placement of the fixture is required. Afterwards, the target placement of the fixture may be determined such that the fixture does not interfere with a neural tube and does not be exposed out of the jawbone. When the target placement of the fixture is determined, a type of the fixture may be determined simultaneously. Design data associated with the target placement of the fixture may be added to the 3D oral cavity image as a part of the 3D oral cavity image.

The oral marker may be attached to an oral cavity of the patient by using an oral marker attachment tool having one or more link arms. Also, the handpiece marker may be attached to the handpiece by using a handpiece marker attachment tool having one or more link arms.

With regard to the attachment of oral marker, the generation of the 3D oral cavity image may include: (a1) applying an impression material to an impression assistant tool which may be partially exposed out of an oral cavity, taking an impression by making the patient to bite the impression material, and acquiring a first base image while the impression is being taken; (a2) acquiring a second base image of the impression assistant tool to which the impression cured and separated from the oral cavity is attached; (a3) preparing an oral gypsum model of the patient, placing the oral gypsum model on a cradle having a predetermined shape and size, and taking a photograph of the oral gypsum model on the cradle to acquire a third base image of the oral gypsum model; and (a4) combining the first through the third base images to generate the 3D oral cavity image.

In such a state, the oral marker may be attached to a portion of the oral gypsum model corresponding to a location of the oral marker attached on the jawbone of the patient, so that each point within the mouth or the 3D oral cavity image can be described by a precise coordinate and be tracked precisely. It is preferable that a first auxiliary marker is attached at a predetermined position in the cradle. The first auxiliary marker may be attached when the oral marker is attached. Alternatively, however, the first auxiliary marker may be attached in advance before the third base image is acquired.

The first auxiliary marker and the oral marker may be photographed by a camera, in a state that the first auxiliary marker and the oral marker are attached on the oral gypsum model, to determine a spatial relationship between the first auxiliary marker and the oral marker.

Once the spatial relationship between the first auxiliary marker and the oral marker is known, it is possible, when the position and the orientation of the oral marker are detected, to determine the position and the orientation of the jawbone from the position and the orientation of the oral marker based on the spatial relationship between the first auxiliary marker and the oral marker.

When the 3D oral cavity image and the handpiece is displayed on a screen, the 3D oral cavity image may be rendered at a viewpoint of a camera or a dentist. At this time, a required translation amount and translation direction, and a required rotation amount and rotation direction of the handpiece may be displayed additionally on the screen. Also, a depth of drilling or a remaining depth may be displayed additionally on the screen.

The implant surgery guide method of the present disclosure can be implemented based on a program stored in a non-transitory computer-readable storage medium and executable by a data processing apparatus.

Advantageous Effects

According to the present disclosure, the placement of the fixture including the position, orientation, and depth of the fixture are guided to the practitioner during the implant procedure. Thus, the present disclosure may greatly reduce the possibility of occurrence of an error and may assure the practitioner that the operation is being performed correctly. Thus, the present disclosure may facilitate the correct implant procedure.

Also, the present disclosure may increase the number of dentists who can perform the implant treatment, enhance therapeutic productivity of each dentist, and reduce the cost of treatment.

DESCRIPTION OF DRAWINGS

In order that the disclosure may be well understood, there will now be described various forms thereof, given by way of example, reference being made to the accompanying drawings, in which:

FIG. 10 illustrates an example of a second CT image of the structure of FIG. 9;

FIG. 11 illustrates an example of an oral gypsum model;

FIGS. 16 and 17 illustrate an example of a merged image of a first vector image and a second vector image, in which FIG. 16 illustrates the merged image of an overall appearance including a face and FIG. 17 illustrates the merged image of a layer associated with the impression assistant tool;

FIG. 33 is a flowchart illustrating a jawbone positioning and rendering process during the implant surgery in an embodiment where only the spatial relationship between the first auxiliary marker and the oral marker is recorded during a marker registration;

FIG. 34 is a flowchart illustrating the jawbone positioning and rendering process during the implant surgery in another embodiment where the coordinates of the jawbone and other oral structures described in a coordinate system of the first auxiliary marker are described again according to a coordinate system of the oral marker during the marker registration;

BEST MODE

Implant Image Guide System

Figure 1:
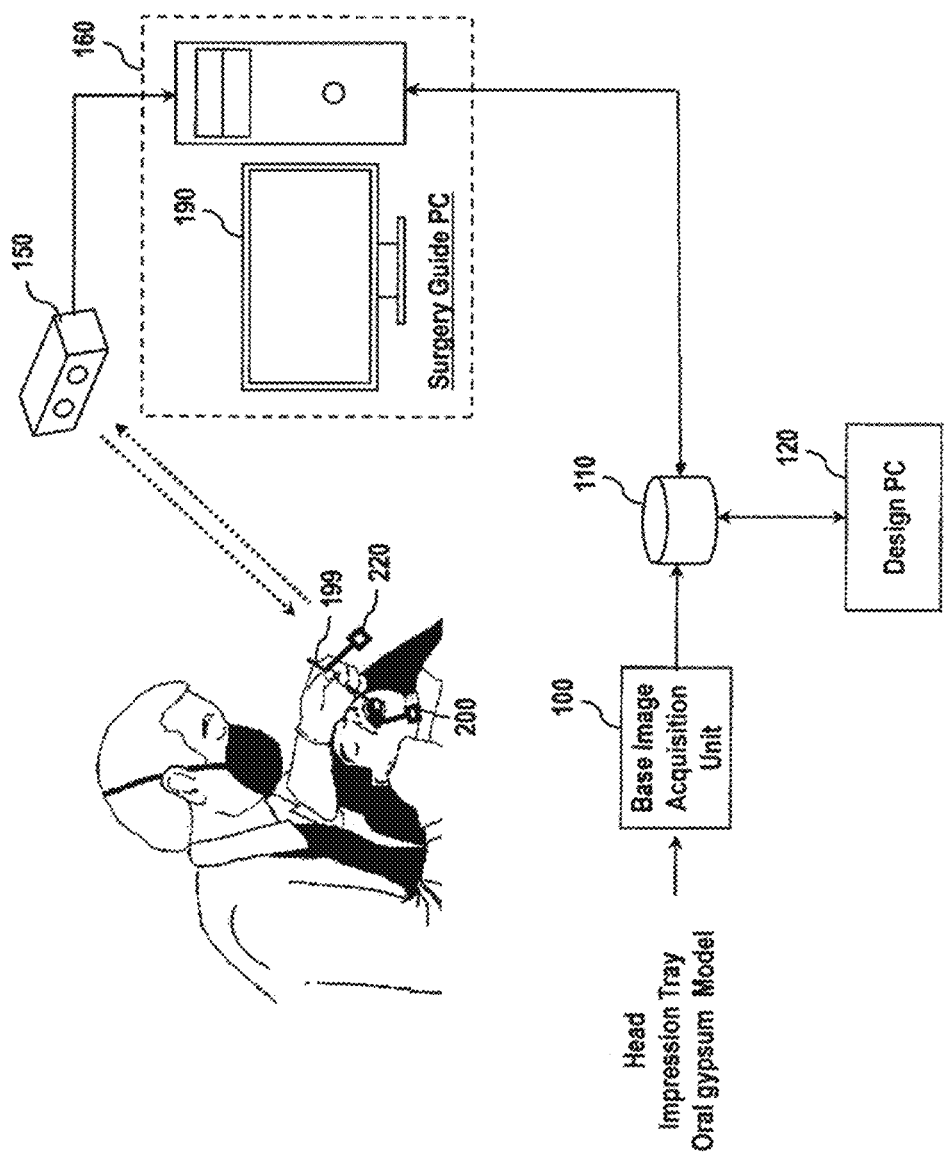
FIG. 1 is a block diagram of an implant image guide system according to an exemplary embodiment of to the present disclosure.

Referring to FIG. 1, an implant image guide system according an exemplary embodiment of to the present disclosure includes a base image acquisition unit 100, a storage unit 110, a design personal computer (PC) 120, the camera sensor 150, and the surgery guide PC 160.

The base image acquisition unit 100 acquires a patient base image of a jawbone and oral cavity before an fixture implant surgery (hereinbelow, referred to as 'implant surgery'). In one embodiment, the base image acquisition unit 100 includes a computed tomography (CT) scanner, and the patient base image acquired by the base image acquisition unit 100 includes CT image of a head including the jaw of the patient. Also, the patient base image may include CT image of an oral gypsum model constructed on the basis of an impressions acquired from the patient's mouth. Here, the CT image may have a data format conforming to a Digital Imaging and Communications in Medicine (DICOM) standard. Meanwhile, the base image acquisition unit 100 may additionally include three-dimensional (3D) scanner of an optical camera type, for example, in addition to the CT scanner. The 3D-scanned image data output by the 3D scanner may have a vector-based stereolithography (STL) format.

The storage unit 110 receives and stores the image data (hereinbelow, referred to as 'base image data'), that is, the CT image data and/or the 3D-scanned image data from the base image acquisition unit 100. As mentioned above, the base image data may be formatted in the DICOM format, and/or at least partly in the STL format. On the other hand, the storage unit 110 receives and stores placement design data output by the design PC 120, which is described below. The placement design data is preferably formatted in the STL format, but the present disclosure is not limited thereto.

The design PC 120 is used to precisely design a target placement of the fixture for one or more teeth defect location based on the base image data stored in the storage unit 110. The term "target placement" is used herein to refer to target positions and target orientations in three-axis directions for each fixture. The design PC 120 stores and executes a design program according to the present disclosure. The design program may convert the data format of the image data formatted in the DICOM format among the base image data stored in the storage unit 110 into the STL format and merge two or more images to generate a 3D oral cavity image. For example, the design PC 120 may merge the CT image or the 3D-scanned image of the oral gypsum model to the head CT image including information on the jawbone and the alveolar bone to form the 3D oral cavity image. Here, the 3D oral cavity image has a form where a precise teeth shape is to the head CT image. The oral cavity image data for the 3D oral cavity image is stored in the storage unit 110. The oral cavity image data is preferably formatted in the STL format, but the present disclosure is not limited thereto. The image format conversion and the merging operations may be regarded as preprocessing operations of arranging the acquired patient base image data rather than a part of the design process although it is described that the design PC 120 is responsible for the operations used for the purpose of simplifying the description of the system configuration.

The design PC 120 also allows a designer to design the target placement of the fixture based in the 3D oral cavity image. The designer may be a dentist, a dental technician, or a member of a dental clinic or a design company. In one embodiment, the design for the target placement of the fixture is achieved by placing a virtual tooth/teeth in the 3D oral cavity image with reference to the standard teeth model, selecting the appropriate fixture among various fixture models, and placing graphic elements for the selected fixture in an appropriate position and in an appropriate orientation in the 3D oral cavity image. Alternatively, however, the design work including the placement of the virtual tooth/teeth, the selection of a fixture, and the placement of graphic elements may be performed automatically by the design program.

The placement design data includes information on a specification of the selected fixture and the target placement of the fixture and is stored in the storage unit 110 for use in an image guide during a surgery. In one embodiment, the placement design data forms a layer added to the 3D oral cavity image and may be merged arbitrarily to the oral cavity image after the design work. However, in order to enhance the understanding of the present disclosure and the present description, it is assumed, as necessary, that placement design data is a separate image or image file from the 3D oral cavity image.

The camera sensor 150 continuously detects the position and orientation of the patient's teeth, the jawbone, or an oral marker 200 attached to a face of the patient during the implant surgery. At the same time, the camera sensor 150 continuously detects the position and orientation of a handpiece marker 220 attached to a handpiece 199 of the dentist. The camera sensor 150 provides real-time position and orientation data of the oral marker 200 and the handpiece marker 220 to the surgery guide PC 160, so that the surgery guide PC 160 can track the jawbone and the handpiece, which may be moving, based on real-time position and orientation data of the oral marker 200 and the handpiece marker 220.

The surgery guide PC 160 may receive the 3D oral cavity image with the placement design data from the storage unit 110 to store in its internal storage medium such as a hard disk or an solid state drive (SSD). In a state that the 3D oral cavity image supplemented with the design data is being displayed on the screen, the surgery guide PC 160 updates and displays the oral cavity and the handpiece in real-time based on the position and orientation data of the oral marker 200 and the handpiece marker 220 from the camera sensor 150, and provides the dental surgeon with additional information to guide the implant surgery.

The surgery guide PC 160 stores and executes the surgical guide program according to the present disclosure. The surgery guide program displays the 3D oral cavity image, particularly the jawbone image portion, on the monitor 190 by superimposing the target placement of the fixture according to the placement design data. Also, the surgery guide program merges or superimposes at least distal portion of the handpiece in the 3D oral cavity image with reference to the position and orientation information of the handpiece determined based on the position and orientation information of the handpiece marker 220 from the camera sensor 150, and displays a merged image on the monitor 190. As a result, the image displayed on the monitor 190 includes the oral cavity including at least the jawbone, the target placement of the fixture, and at least distal portion of the handpiece.

Further, the surgery guide program determines the real-time motion of the jawbone based on the position and orientation information of the oral marker 200, and translates and/or rotates, in real-time, the jawbone portion and the fixture placement portion of the image displayed on the monitor 190 based on the determined motion of the jawbone. Similarly, the surgery guide program determines the real-time motion of the handpiece based on the position and orientation information of the handpiece marker 200, and translates and/or rotates, in real-time, the handpiece portion of the image displayed on the monitor 190 based on the determined motion of the handpiece. Thus, the surgery guide program allows the image displayed on the monitor 190 to accurately reflect the motion of the jawbone and the handpiece.

Figure 2:
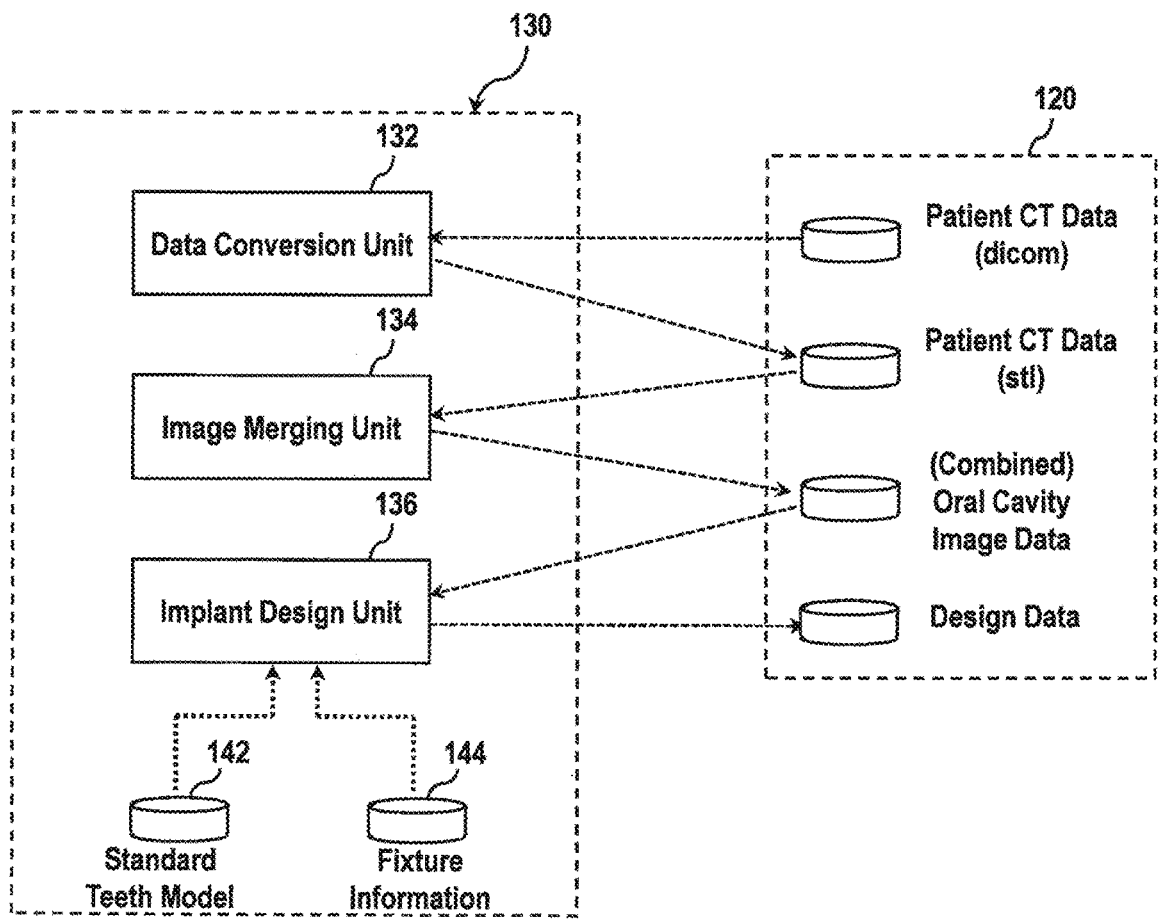
FIG. 2 is a block diagram of an exemplary embodiment of a design program executed in a design PC shown in FIG. 1.

FIG. 2 illustrates an exemplary embodiment of the design program executed in the design PC 120. In the illustrated embodiment, the design program 130 includes a data conversion unit 132, an image merging unit 134, and an implant design unit 136. Also, the design program 130 may include a standard teeth model table 142 and a fixture information table 144. The standard teeth model table 142 stores statistical standard model information for relative positional relationship or arrangement between each tooth, size of each tooth, and axial orientation of each tooth, which are defined in advance. Here, the statistical standard model may be a model recognized anthropologically or anatomically and commonly admitted in the dental science community, or a model established by a system operator of the present disclosure empirically and accumulatively. The fixture information table 144 preferably stores information about inner diameters, lengths, and outer shapes of almost all the commercially available fixtures.

The data conversion unit 132 converts the format of the patient's base image data stored in the storage unit 110 into a certain format, e.g., the STL format. Accordingly, all the CT data in the DICOM format can be converted into the STL format. If some of the base images are acquired by the 3D scanner and are formatted in the STL, such data can also be converted to the STL format.

The image merging unit 134 merges or merges two or more 3D images formatted in the STL format into a single image file. As mentioned above, one example of the image merging is to merge the image of the oral gypsum model to the head CT image containing information on the jawbone and the alveolar bone so as to acquire the head CT image supplemented with a precise teeth shape. The purpose and specific examples of the image merging are described in detail below.

The implant design unit 136 allows a designer to determine the target placement, based in the 3D oral cavity image of the STL format, taking into account the position and thickness of the alveolar bone and without touching nerves. In particular, the implant design unit 136 allows the designer to dispose virtual tooth at a tooth location to be treated takes into account the corresponding relationship between the patient's teeth arrangement and the standard teeth model 142, select an appropriate one among the various fixtures, and place the graphic elements for the selected fixture in an appropriate position and in an appropriate orientation in the 3D oral cavity image. In this process, the implant design unit 136 allows the designer to determine a fixture having a certain size or type among the various product information stored in the fixture information table 144. The design data determined by the implant design unit 136, which is stored in the storage unit 110, includes the target placement of the fixture (i.e. the information about the target position and the target orientation) and the specification data of the selected fixture.

In one embodiment, the design program 130 performs the operations of the format conversion, the image merging, and the arrangement of the graphic element based on an instruction input by the designer. Alternatively, however, the design program 130 may automatically perform the operations of the format conversion, the image merging, and the arrangement of the graphic element.

Figure 3:
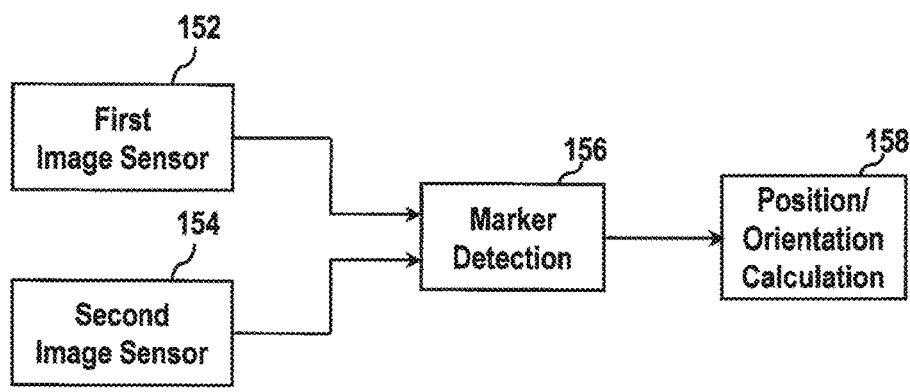
FIG. 3 is a block diagram of an exemplary embodiment of a camera sensor shown in FIG. 1.

FIG. 3 illustrates an exemplary embodiment of the camera sensor 150 shown in FIG. 1. In the illustrated embodiment, the camera sensor 150 includes a first image sensor 152, a second image sensor 154, a marker detection unit 156, and a position/orientation calculation unit 158. Preferably, the first and second image sensors 152 and 154 form a stereoscopic camera, but the present disclosure is not necessarily limited thereto. The first and second image sensors 152 and 154 may be installed such that the oral marker 200 attached to or near the patient's jawbone and the handpiece marker 220 attached to the handpiece 199 is included in their angles of view so as to continuously capture the oral marker 200 and the handpiece marker 220. The marker detection unit 156 detects the oral marker 200 and the handpiece marker 220 in the output images of the first and second image sensors 152 and 154. The position/orientation calculating unit 158 calculates the positions and orientations of the oral marker 200 and the handpiece marker 220. As time goes on, the camera sensor 150 repeatedly carries out the image capture, the marker detection, and the calculation of the positions and orientations of the markers 200 and 220, and the positions and orientations information of the oral marker 200 and the handpiece marker 220 are transmitted to the surgery guide PC 160. Although it is not shown in the drawing, it is preferable that the camera sensor 150 is provided with an infrared illumination in order to eliminate the sensitivity variation according to the luminance level.

Figure 4:
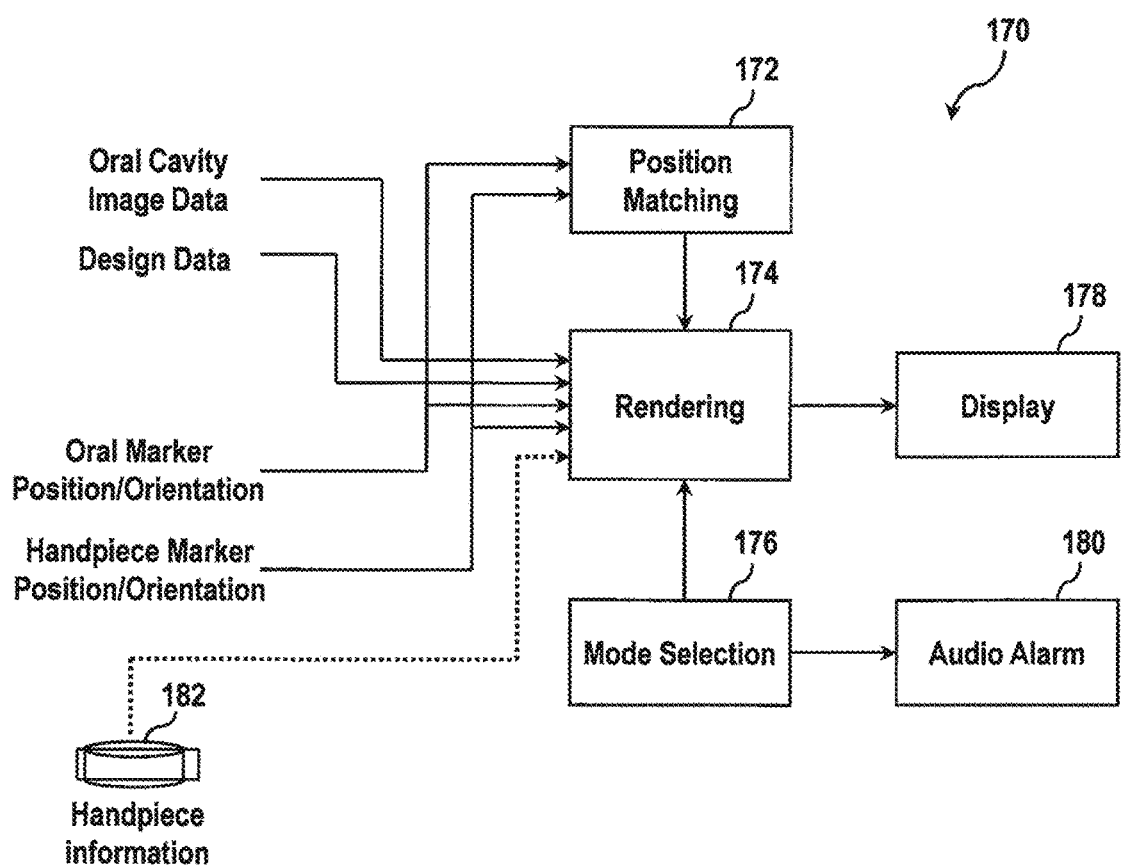
FIG. 4 is a block diagram of an exemplary embodiment of a surgical guide program executed in a surgical guide PC shown in FIG. 1.

FIG. 4 illustrates an exemplary embodiment of a surgical guide program 170 executed in the surgical guide PC 160 shown in FIG. 1. In the illustrated embodiment, the surgery guide program 170 includes a position matching unit 172, a rendering unit 174, a mode selection unit 176, a display unit 178, and a audio alarm unit 180. Also, the surgery guide program 170 may include a handpiece information table 182 that stores information on sizes, other specifications, and 3D image data of commercially available handpieces.

The position matching unit 172 integrates the 3D oral cavity image portion of the patient and the handpiece image portion into a single universal coordinate system, for example, into a camera sensor coordinate system at the beginning of the implant surgery, so that the pixels of all the objects may be displayed uniformly according to a single universal coordinate system on the monitor 190.

The rendering unit 174 renders the 3D oral cavity image to which the design data is supplemented. Here, it is preferable that the oral cavity portion around the jawbone in which the implant surgery is performed is enlarged on the monitor 190. The rendering unit 174 renders a display image in such a manner that the 3D handpiece image is superimposed to the 3D oral cavity image the monitor 190 on the basis of the 3D handpiece image data stored in the handpiece information table 182 and the position and orientation information of the handpiece marker 220. Also, the rendering unit 174 determines the real-time motion of the jawbone based on the position and orientation information of the oral marker 200, and translates and/or rotates, in real-time, the jawbone portion and the fixture placement portion of the image displayed on the monitor 190 based on the determined motion of the jawbone. Similarly, the rendering unit 174 determines the real-time motion of the handpiece based on the position and orientation information of the handpiece marker 200, and translates and/or rotates, in real-time, the handpiece portion of the image displayed on the monitor 190 based on the determined motion of the handpiece. Thus, the rendering unit 174 allows the image displayed on the monitor 190 to accurately reflect the motion of the jawbone and the handpiece.

The mode selection unit 176 allows the dentist or a hygienist to adjust a view of the image displayed on the screen and choose any additional information to be displayed on the screen. The display unit 178 stores the image data generated by the rendering unit 174 in a frame memory (not shown) so that an image corresponding to the image data stored in the frame memory is displayed on the monitor 190. The audio alarm unit 180 outputs a beep or a audio guidance during the surgery according to an operation mode setting. The audio alarm unit 180 may be, for example, a speaker, a headphone, or a headset.

The camera sensor 150 and the surgery guide PC 160 shown in FIG. 1 are installed in a dental clinic performing the implant surgery. In one embodiment, the base image acquisition unit 100, the storage unit 110, and the design PC 120 may be installed in the dental clinic that performs the implant surgery, so that the acquisition of the jawbone state of the patient and the design process may be performed in the dental clinic performing the implant surgery. Alternatively, however, the design PC 120 may be installed in an external design center, where professional designers perform the design work and provide the dental clinic with the design data through a network. Also, at least a portion of the base image acquisition unit 100, e.g., the CT scanner, may be provided in a separate radiology clinic or a centralized CT imaging center. In such case, the design PC 120 may receive the CT image data from the CT scanner online through the network.

The implant surgery guiding method according to an exemplary embodiment of the present disclosure will now be described in detail.

Overall Procedure

Figure 5:
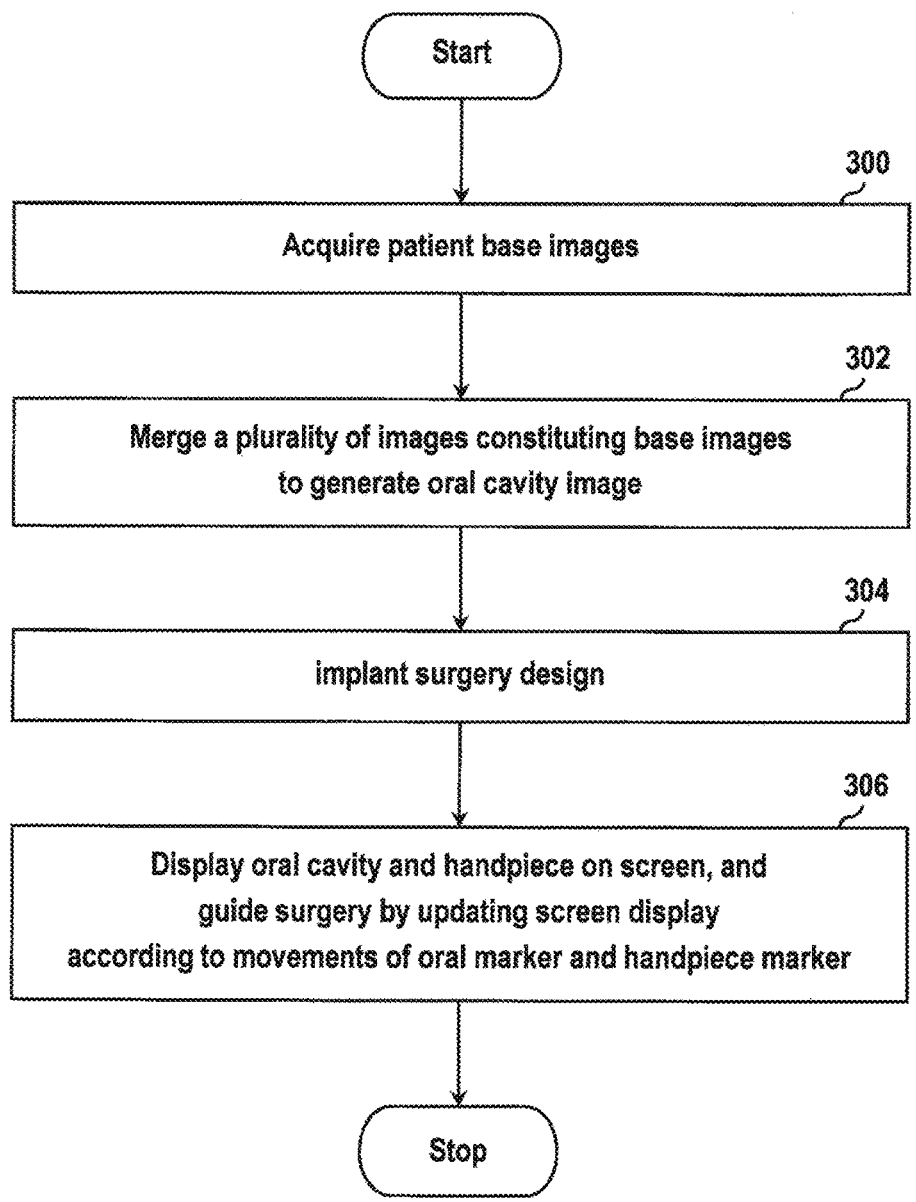
FIG. 5 is a flowchart schematically showing an overall process of an implant surgery guiding method according to an exemplary embodiment of the present disclosure.

FIG. 5 schematically illustrates an overall process of an implant surgery guiding method according to an exemplary embodiment of the present disclosure.

The implant surgery guiding method is based on the image information such as the 3D head image. While the CT image of the head including the teeth and the jaws has information on the overall skull structure and the shape of the jawbones, but the detailed position and contour of individual tooth which is one of the most important factors cannot be extracted from the CT image. This shortcoming may come from a low resolution of the CT image. In particular, patients who have undergone prosthetic treatment with a metal prosthesis such as gold can experience light scattering in the metal prosthesis, which deteriorates the precision of the CT image. As a result, a single CT scan cannot guarantee the acquisition of necessary information. Thus, according to a preferred embodiment, a plurality of the patient base images are acquired and merged to produce the 3D oral cavity image encompassing the teeth and the jaws.

In operation 300, the base images of the jawbone and the oral cavity of the patient who is to be subject to the implant surgery are acquired. The patient base images can be acquired, for example, by the CT scans of the patient's jawbone and the oral cavity using the CT scanner. Some of the images may be acquired by the 3D scanner rather than the CT scanner. Then, a plurality of images constituting the base image are merged to generate the 3D oral cavity image (operation 302).

Next, the surgery design or planning process is performed by selecting the type of fixture and the target placement of the fixture by using the design PC 120, thereby determining the type of the fixture, the target position and the target orientation of the fixture (operation 304).

After the surgery design process is completed, the handpiece image is displayed on the screen together with the 3D oral cavity image including the fixture target placement while the implant fixture placement is performed on the patient, and the implant surgery guide is performed by updating the screen display according to the movement of the oral marker 200 and the handpiece marker 220 while tracking the movements of the markers 200 and 220 (operation 306).

The operations 300-304 shown in FIG. 5 may be regarded as preliminary preparations for generating base data for the surgery guide prior to the implant surgery.

Acquisition of the Patient Base Image

According to an embodiment, a plurality of CT images are acquired as the patient base images. During the imaging of the plurality of CT images, an impression of the patient's teeth is taken. At this time, an impression assistant tool according to the present disclosure is utilized in order to facilitate the process of merging the plurality of CT images into a single image at a later time.

Figure 6:
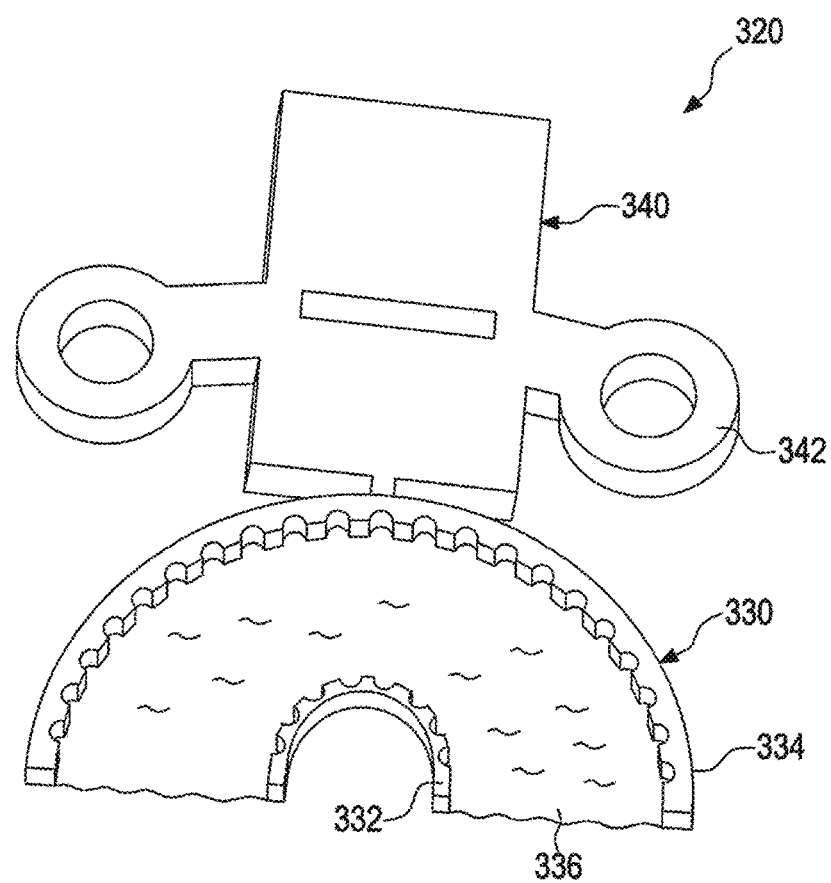
FIG. 6 illustrates an impression assistant tool according to an exemplary embodiment of the present disclosure.

FIG. 6 illustrates the impression assistant tool according to an exemplary embodiment of the present disclosure.

The impression assistant tool 320 shown in FIG. 6, which is manufactured based on an impression tray typically used in taking an impression in a dental clinic, includes an impression material receiving portion 330 configured to correspond to a teeth arrangement and a handle 340 extending outwards from the impression material receiving portion 330.

The impression material receiving portion 330 has an inner wall 332, an outer wall 334, and a screen 336. The inner wall 332 extends in a vertical direction and has an arch-shaped horizontal cross-section. The outer wall 334 is spaced apart outwardly from the inner wall 332, extends in the vertical direction, and has an arch-shaped horizontal cross-section. The screen 336 connects an outer surface of the inner wall 332 to an inner surface of the outer wall 334. Due to the inner wall 332, the outer wall 334, and the screen 336, the impression material receiving portion 330 has a upper channel and a lower channel having a U-shaped and an inverted U-shaped cross-section, respectively, and allows a practitioner to simultaneously take the impressions for both teeth sets in the maxilla and the mandible.

On the outer surface of the inner wall 332 and the inner surface of the outer wall 334, provided are ribs extending vertically to minimize any movement, separation, or warpage of the impression material in the impression taking process. The screen 336, which may be made of a nonwoven fabric woven from a sufficiently thin sheet of soft material such as a cotton gauze, a nylon mesh, or polyether, works as a retaining base for the impression material and minimizes any interference with the patient's teeth during an occlusion and prevents precise occlusion of the upper and lower teeth.

The handle 340 is attached to an outer surface of the outer wall 334 of the impression material receiving portion 330. The edges of the handle 340 preferable includes symmetrical elements, asymmetric elements, straight lines, and curves, so as to be recognized precisely while the plurality of CT images are merged into a single image later. For example, in FIG. 6, a ring-shaped protrusion 342 is formed laterally outwards from a substantially rectangular parallelepiped-shaped handle body. In the image merging process described later in detail, the curved and straight corners of the handle 340 serve as characteristic geometry elements for recognizing the spatial positions and orientations of the planes in the CT images. It is to be noted, however, that the shape of the handle 340 is not limited to that shown in FIG. 6.

Figure 7:
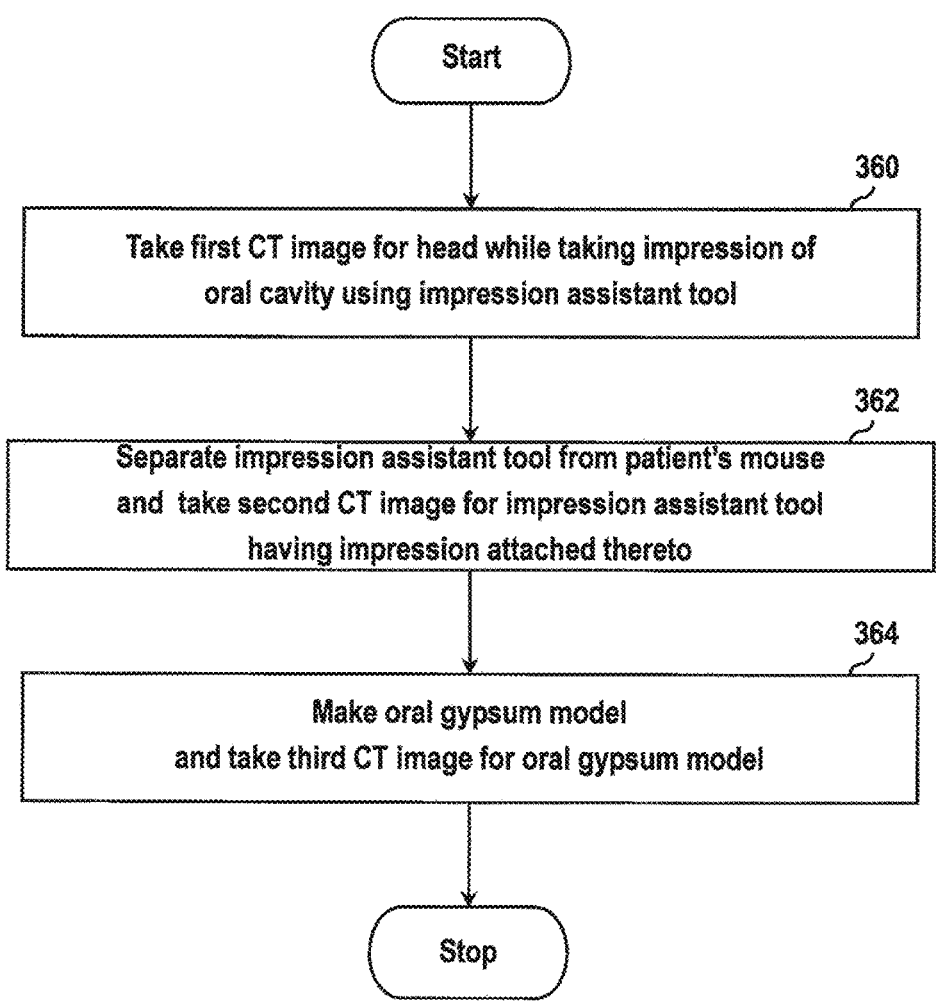
FIG. 7 is a flowchart illustrating a process of acquiring patient base images according to an exemplary embodiment of the present disclosure.

FIG. 7 illustrates the process of acquiring the patient base images, in detail, according to an exemplary embodiment of the present disclosure;

First, a first CT image of the head is acquired using the impression assistant tool 320 shown in FIG. 6 while taking impressions of the maxilla and mandible (operation 360). The most fundamental one of the patient base images is the 3D image of the patient's jawbone. In a preferred embodiment, the 3D image of the patient's jawbone is acquired by taking the CT image of the head including the jawbone. At this time, the CT image of the head may be taken with an emphasis on either the maxilla or the mandible which requires the treatment.

The first CT image is taken by use of the impression assistant tool 320, to facilitate the merging with other images, while taking the impression for the patient's mouth. The impression is taken by use of the impression assistant tool 320 by applying a sufficient amount of the impression material to the upper and lower channels of the impression assistant tool 320 so as to simultaneously take the impressions for both teeth sets in the maxilla and the mandible. Any suitable impression materials commercially available or known in this field such as alginate, polyvinylsiloxane, polyether, and super-hydrophilic vinyl polysiloxane, or a merging of two or more of them may be used.

Figure 8:
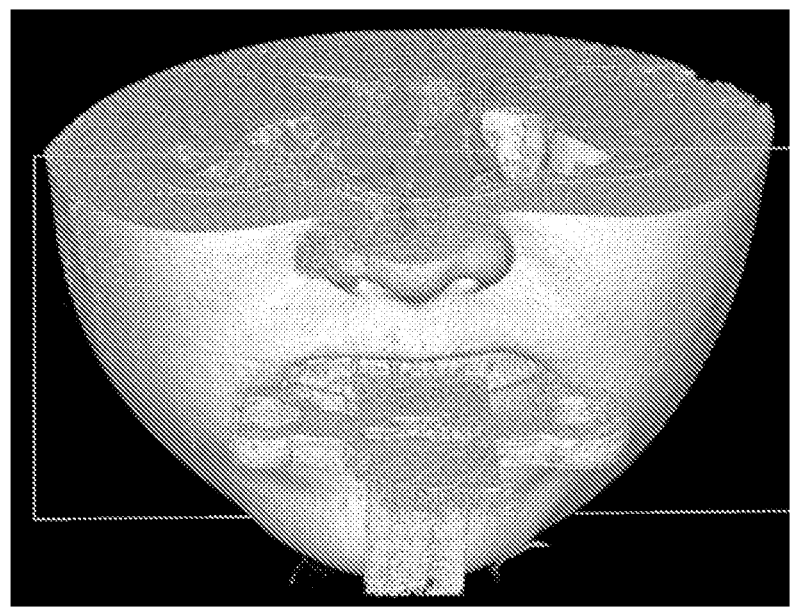
FIG. 8 illustrates an example of a first CT image.

The first CT image may be taken after the impression material is cured or during a curing process. Meanwhile, during the impression taking process, the patient does not have to bite the impression assistant tool 320 such that the handle 340 is directed to a front direction, but may bite the impression assistant tool 320 such that the handle 340 is oriented in an oblique direction. FIG. 8 shows an example of the first CT image. As shown in the drawing, the first CT image is an image of a face in a state that the patient is biting the impression assistant tool 320 during the impression taking step. It is possible to extract only a skull layer excluding skin tissues from this normal CT image of the head as necessary.

Figure 9:
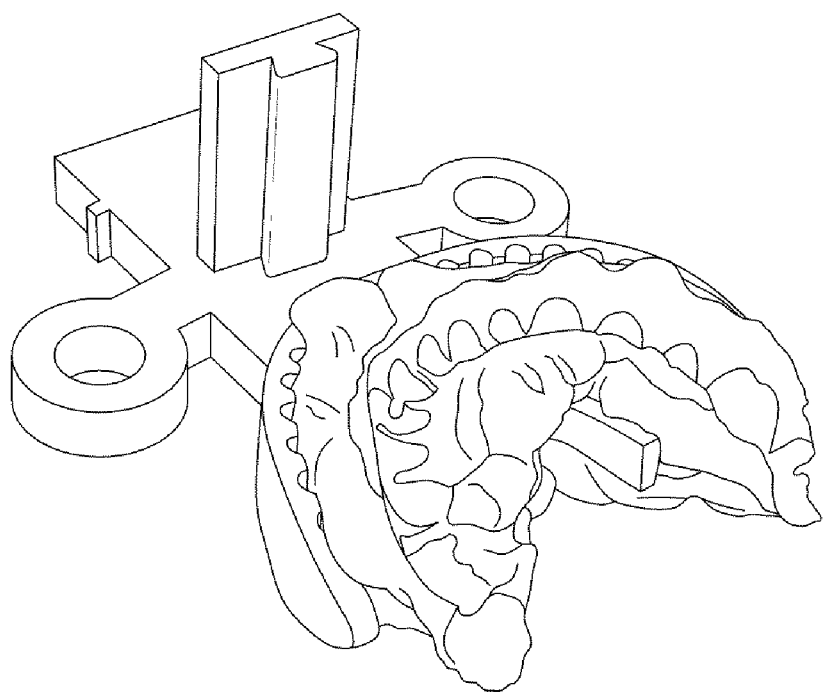
FIG. 9 illustrates an example of the impression assistant tool having an impression attached thereto.

After a sufficient time has elapsed to allow the impression material to harden, the impression assistant tool 320 is separated from the patient's mouth. As shown in FIG. 9, the impression having a negative imprint of the upper and lower teeth of the patient is attached to the separated impression assistant tool 320. In operation 362, a second CT image is taken separately for the impression assistant tool 320 with the impression attached thereto. FIG. 10 illustrates an example of the second CT image of the impression assistant tool 320 with the impression attached thereto.

In operation 364, the oral gypsum model is prepared and a third CT image is taken for the oral gypsum model. The oral gypsum model may be made using the impression made in the process of taking the first and second CT images. However, the impression may not fully reflect the teeth because of several reasons. For example, the patient's teeth may move or twist while the impression and the CT images are taken. Also, the impression material may be filled insufficiently, particularly near the edges of the molar teeth while the impressions are simultaneously taken for both the maxilla and the mandible. Accordingly, the impression taken in the process of acquiring the first and second CT images may show a low precision. In view of this, in a preferred embodiment, a new impression may be taken for the entire teeth in the maxilla or the mandible or around the tooth requiring the treatment using a separate impression tray. Then, the oral gypsum model may be made using the new impression, and the third CT image may be taken for the new oral gypsum model. FIG. 11 illustrates an example of the oral gypsum model which is made using the new impression. In FIG. 11, the oral gypsum model in the left is the model for the maxilla and the oral gypsum model in the left is the model for the mandible.

Figure 12:
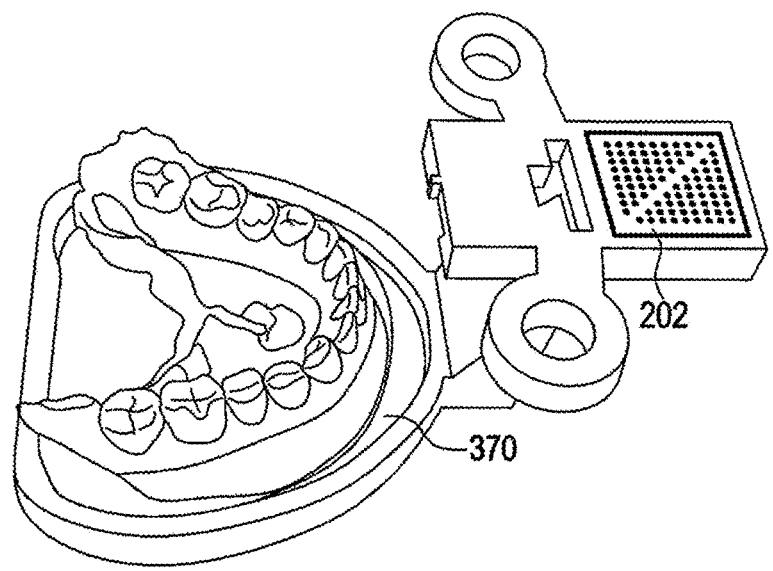
FIG. 12 illustrates the oral gypsum model for a mandible in a state of being placed on a cradle for taking a third CT image according to an exemplary embodiment of the present disclosure.

Meanwhile, when the third CT image of the oral gypsum model is taken, the oral gypsum model may placed on a prescribed cradle. FIG. 12 shows a state that the oral gypsum model the mandible is placed on the cradle. The shape and size of the cradle 370 are preferably stored in the design PC 120 shown in FIG. 1 in the form of the 3D image. It is preferable that an auxiliary marker 202 is attached to a position of the cradle 370. In the drawing, the portion of the cradle 370 where auxiliary marker 202 is attached seems to have a shape similar to that of the handle 340 of the impression assistant tool 320. This is because the impression assistant tool 320 and the cradle 370, which are made by way of examples, were prepared from design data similar to each other for the sake of easy processing using a 3D printer. However, the shape of the portion of the cradle 370 to which the auxiliary marker 202 is attached is not necessarily the same as the shape of the handle 340 of the impression assistant tool 320.

The cradle 370 does not have to have a specific shape. However, for the convenience of recognition in the design PC 120, it is desirable that the shape of the cradle 370 is kept uniformly. Also, when a plurality of cradles 370 are manufactured, it is preferable to attach the auxiliary markers 202 in the same position for each cradle 370 for facilitating the position registration or the integration of the coordinate systems in an initial stage of the surgical guide, which is described below. The oral gypsum model may be fixed at an arbitrary position on the cradle 370 using the gypsum or another adhesive before taking the CT image. Thus, in the preferred embodiment, the object for which the CT image is taken in the operation 364 is the gypsum model fixed on the cradle 370 to which the auxiliary marker 202 is attached. At this time, the CT image is taken to include at least a portion of the cradle 370. The use of the auxiliary marker and additional functions of the cradle will be described in detail below with respect to the image merging and the surgery image guide.

Figure 13:
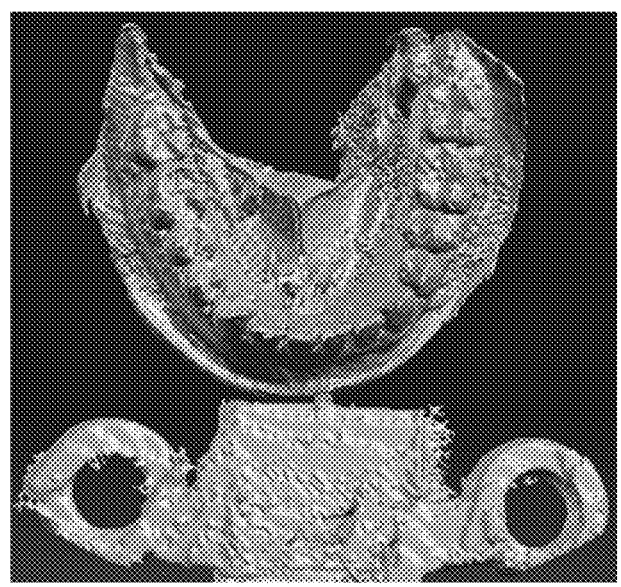
FIG. 13 illustrates an example of a third CT image of the mandible.
Figure 14:
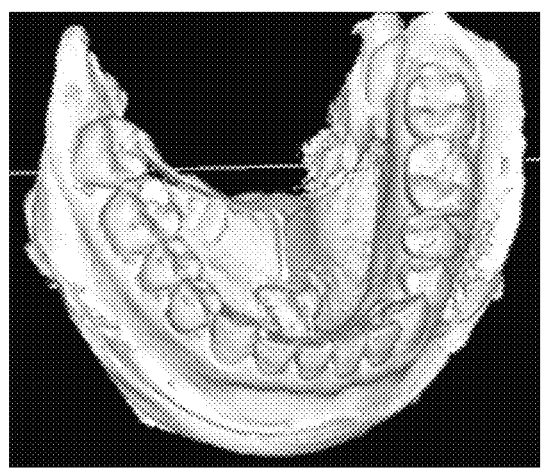
FIG. 14 illustrates a teeth portion extracted from the third CT image.

FIG. 13 shows an example of the third CT image of the mandible taken in the state shown in FIG. 12. FIG. 14 illustrates a teeth portion extracted from the third CT image excluding a portion of the cradle. As shown in the drawing, the third CT image includes the teeth and a gingiva in the mandible.

Merging Images

Figure 15:
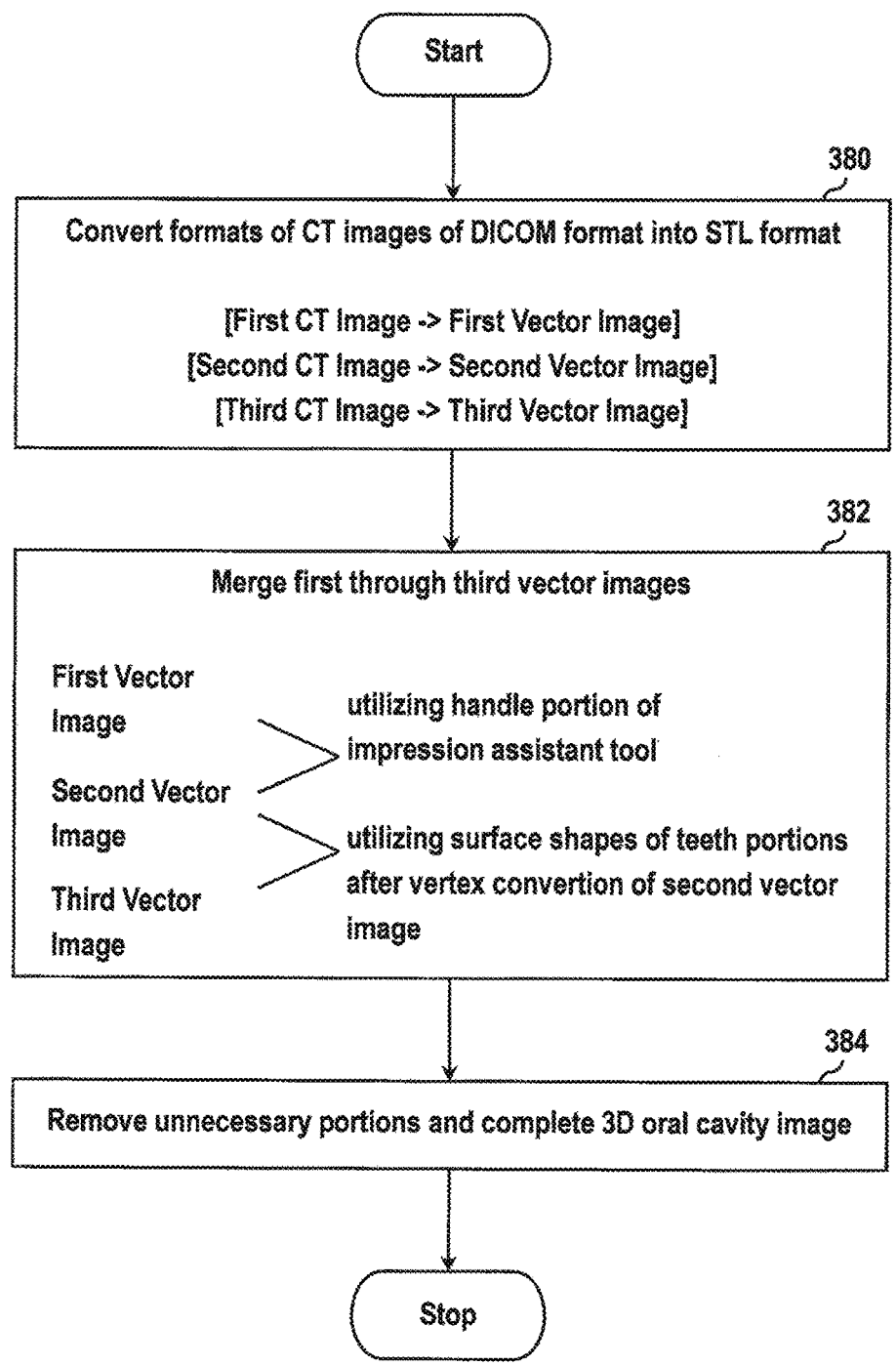
FIG. 15 is a flowchart illustrating an image merging process according to an exemplary embodiment of the present disclosure.

FIG. 15 illustrates the image merging process according to an exemplary embodiment of the present disclosure.

The data conversion unit 132 of the design program 130 in the design PC 120 converts the formats of the patient base images stored in the storage unit 110 into the STL format, for example, in operation 380. Accordingly, all the CT data in the DICOM format can be converted into the STL format. If the first through third CT images are formatted in the DICOM format as in the embodiment described above, the data conversion unit 132 converts the first through third CT images into the STL format. In the following description, the first through third CT images converted into the STL format are referred to as a first through third vector images, respectively.

Subsequently, the image merging unit 134 of the design program 130 combines or merges the first through third vector images into a single 3D image (operation 382).

The second vector image and the third vector image are combined using respective surface shape information of the teeth portion. First, since the teeth and the gingiva are negatively imprinted in the impression body and reflected in an intaglio in the second vector image, the image merging unit 134 converts the vertices of the teeth and the gingiva into a positively representing emboss shape. For example, the mandible and the mandible are engraved into respective impressions before the vertex conversion, but protrudes from the jawbones similarly to real teeth after the vertex conversion. Thus, the second vector image after the vertex conversion is similar to the third vector image in the teeth and the gingival portions, but differs from the third vector image only in the precision of the surface texture and the shapes of the edges. Therefore, it is possible to combine the second vector image and the third vector image using their surface curvatures, i.e. their surface shapes after the vertex conversion. At this time, the vertices and vectors are mainly used for the merging of the images. However, it is possible to use unique edges or curves together with or instead of the vertices and vectors.

On the other hand, the first vector image and the second vector image have common portions of the handle 340 shown in FIG. 6, and are combined using the common portions of the handle 340.

Figure 16:
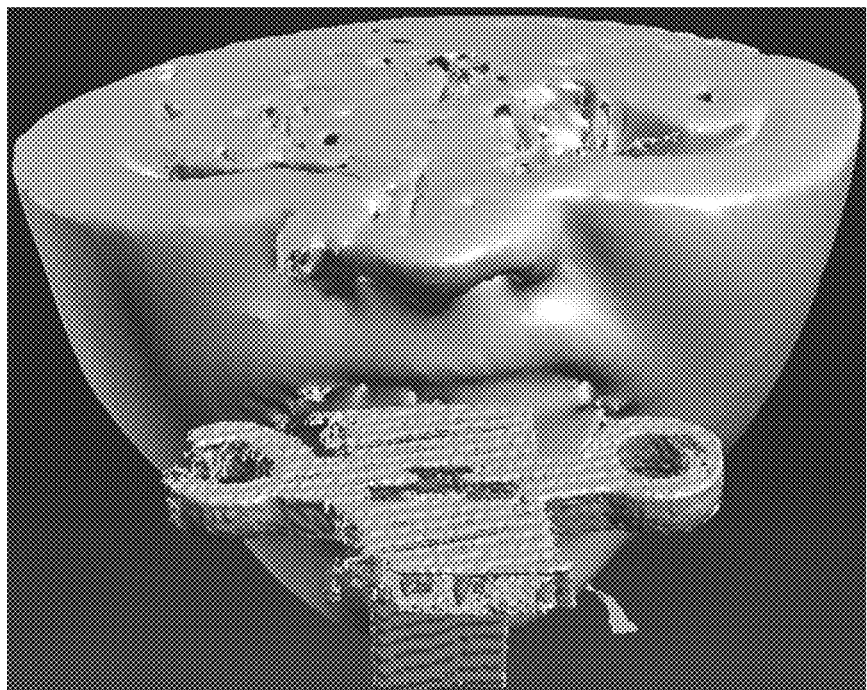
Figure 17:
Figure 18:
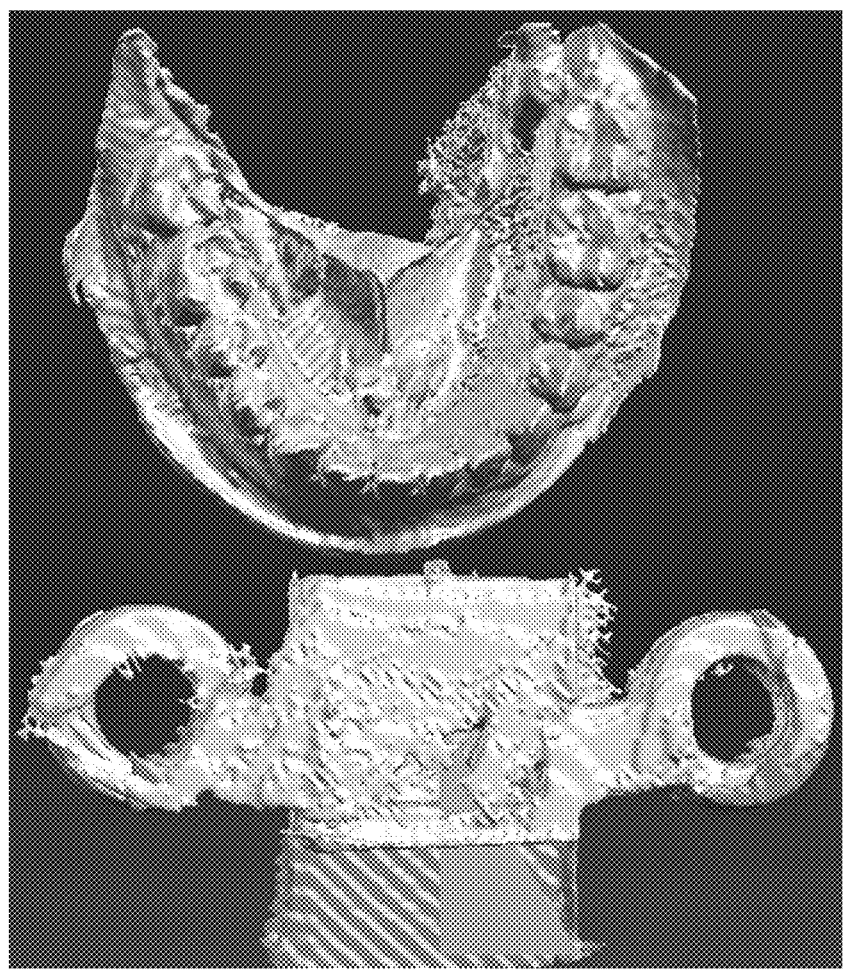
FIG. 18 illustrates an example of a merged image of the second vector image and a third vector image.

FIGS. 16 and 17 illustrate an example of a merged image of the first vector image and the second vector image. In particular, FIG. 16 illustrates the merged image for an overall appearance including a face, and FIG. 17 illustrates the merged image of a layer associated with the impression assistant tool. FIG. 18 illustrates an example of a merged image of the second vector image and the third vector image.

In one embodiment, the second and third vector images are combined after the vertex conversion of the second vector image, and then the first vector image is merged additionally. However, the sequence of merging the first through third vector images is not limited to this, and the designer may arbitrarily determined which images are to be merged first. That is, instead of merging the second and third vector images and then further merging the first vector image, it is possible to merge the first and second vector images and then merge the third vector image.

Finally, unnecessary portions including the portion of the handle 340 of the impression assistant tool 320 are removed from the merged image to complete the 3D oral cavity image (operation 384).

Facial skin, the skull, the maxilla, the mandible, the teeth, the gingiva, and the alveolar bone are shown in the 3D oral cavity image. Further, each of the facial skin, the skull, the maxilla, the mandible, and a neural tube may be selectively displayed in a separate layer or be excluded from the display. Though the CT images of the head may be insufficient for extracting detailed positions and contours of individual tooth as described above, the 3D oral cavity image contains information about the overall head structure and the shape of the jawbones as well as precise teeth information supplemented by the three-dimensional gypsum model data.

Furthermore, it is possible to describe an arbitrary position, in the oral cavity and the skull including the jawbones (i.e., the maxilla and/or the mandible), the teeth, the gingiva, and the alveolar bone in the 3D oral cavity image, by a coordinate according to a single universal coordinate system. The origin of the universal coordinate system and the direction of each axis may be determined arbitrarily. For example, in case that the size and shape of the cradle 370 are kept uniformly and the auxiliary marker 202 is attached in the same position for each cradle 370, the auxiliary marker 202 would be located in a constant position and in a constant orientation in the single universal coordinate system and any point in or on the auxiliary marker 202 may be set to be the origin of the coordinate system.

Implant Surgery Design

Figure 19:
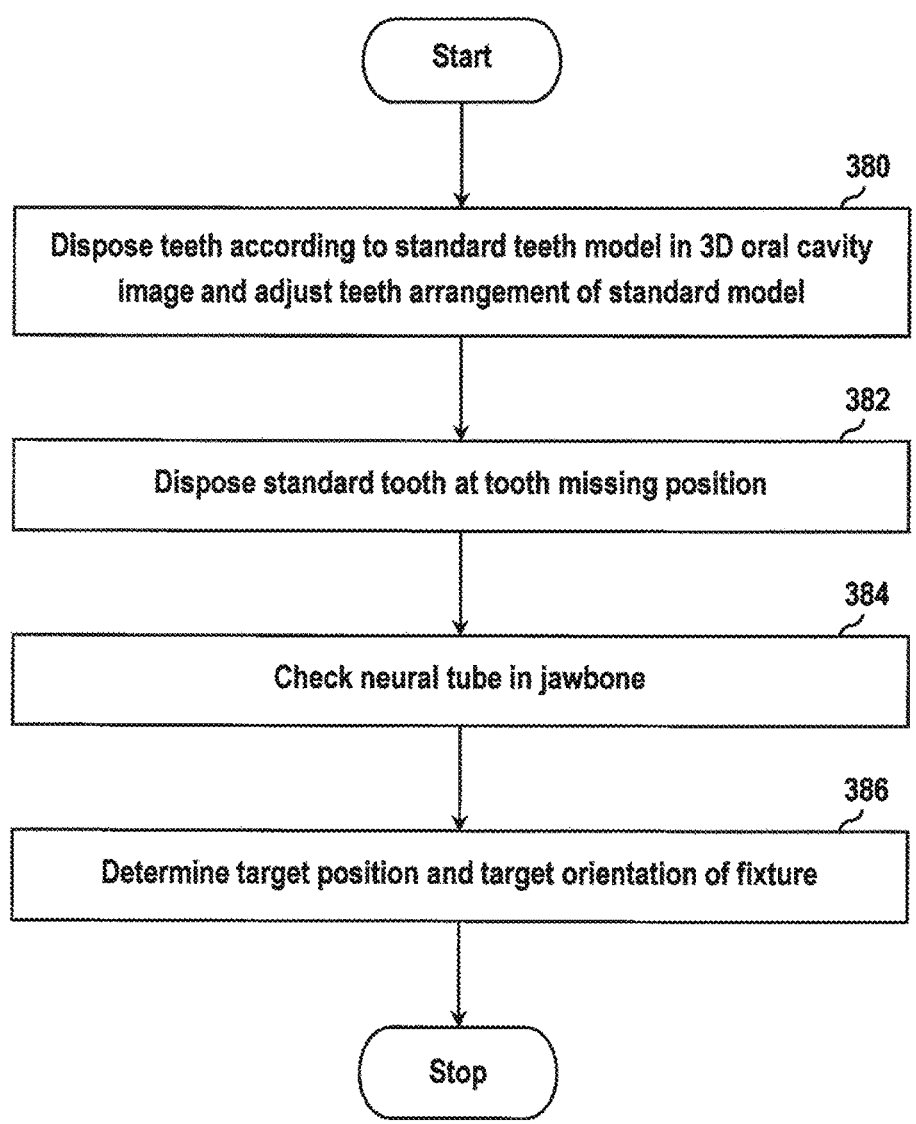
FIG. 19 is a flowchart illustrating an implant design process according to an exemplary embodiment of the present disclosure.

FIG. 19 illustrates the surgery design process according to an exemplary embodiment of the present disclosure in detail.

Figure 20:
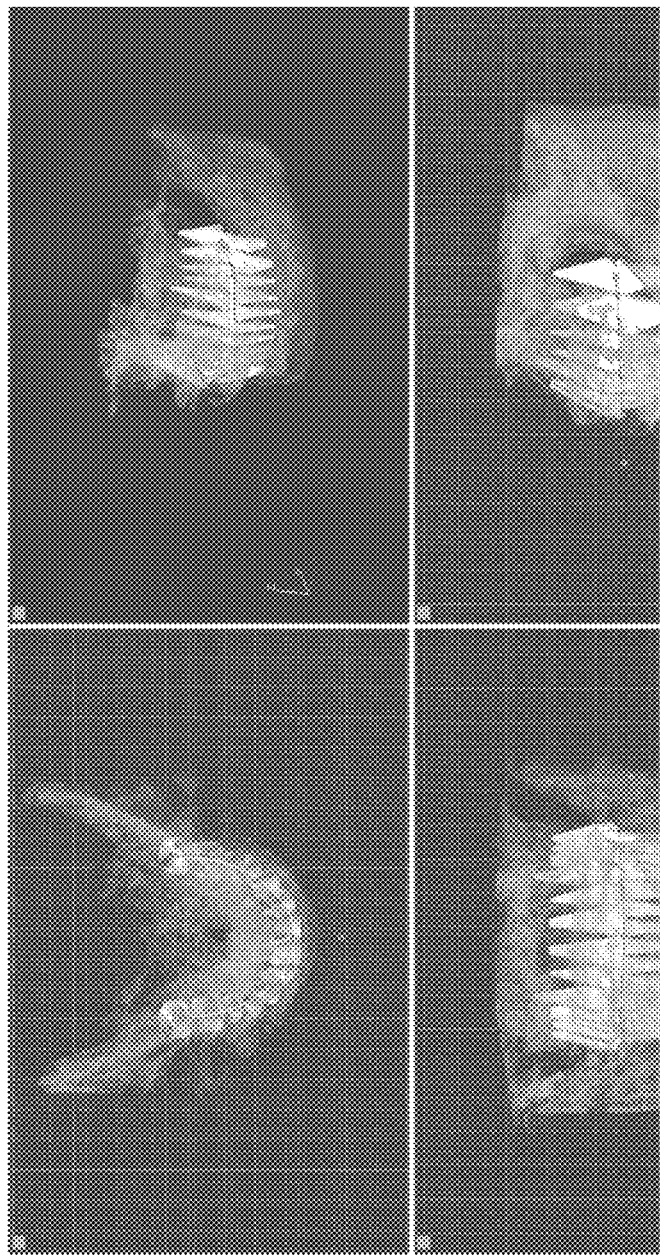
FIG. 20 is an exemplary screenshot of a screen in which teeth according to a standard teeth model is superimposed on a three-dimensional oral cavity image of a patient.

First, the teeth according to the standard teeth model is disposed in the 3D oral cavity image of the patient, and the teeth arrangement of the standard teeth model is adjusted according to the patient's remaining teeth and/or the alveolar bone (operation 380). FIG. 20 is an exemplary screenshot of a screen in which teeth according to the standard teeth model is superimposed in the 3D oral cavity image of the patient. The adjustment of the teeth arrangement of the standard teeth model can be performed by mouse-dragging the vertices or control points shown in FIG. 20.

Afterwards, a standard tooth conforming to the standard teeth model is disposed at a tooth missing location where the implant is required and the other teeth in the standard teeth model are excluded at least temporarily (operation 382).

Next, the position of the neural tube in the jawbone is checked (operation 384). The position of the neural tube can be checked from the first CT image. As described above, neural tube may be discriminated by a separate layer the facial skin, the skull, the maxilla, and the mandible in the 3D oral cavity image to be selectively displayed layer or selectively be excluded from the display.

Figure 21:
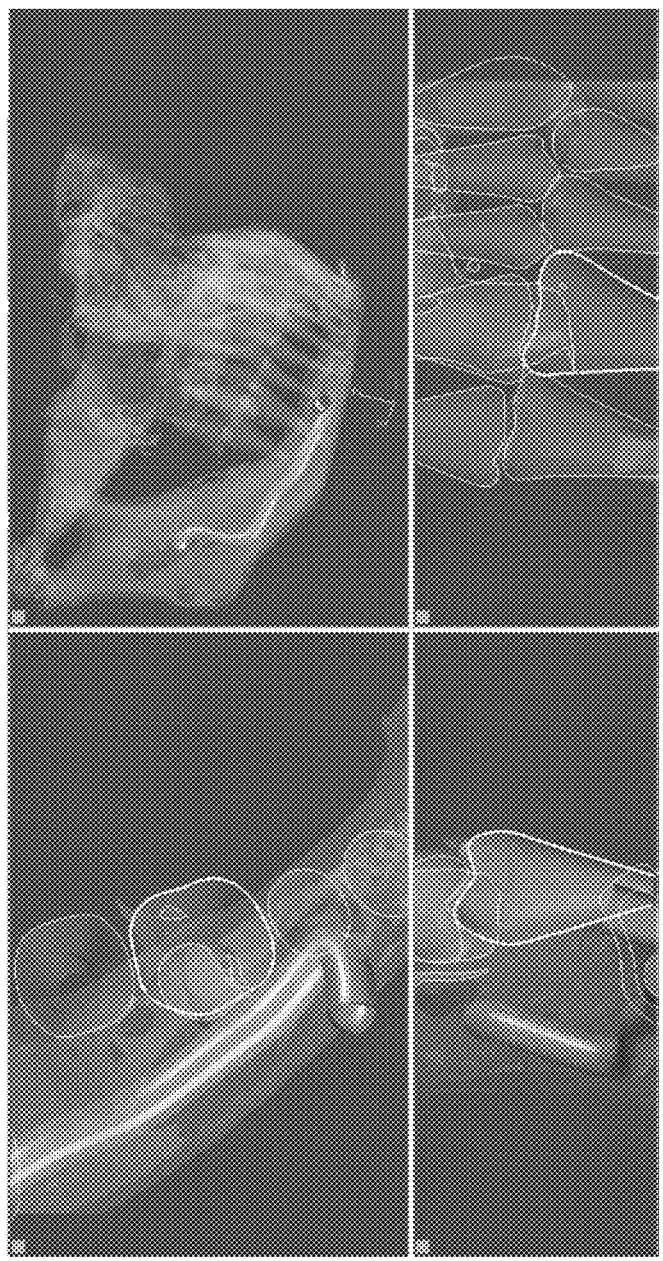
FIG. 21 is an exemplary screenshot of a screen for determining a target position and a target orientation of a fixture.

In operation 386, the target position and the target orientation of the fixture are determined. The determination of the target position and the target orientation of the fixture is made by translating or rotating the fixture within the screen. In determining the target position and the target orientation, the center axis of the fixture is arranged to be aligned with the center axis of the standard tooth disposed in the operation 382, or at least not to be significantly deviated from the standard tooth. Also, the fixture is positioned such that the fixture does not interfere with the neural tube and does not be exposed over the inner or outer wall of the jaw but be stably placed in the jaw. If the jaw is thin or the fixture is likely to interfere with the neural tube, the thickness and/or the length of the fixture is changed. FIG. 21 shows an exemplary screenshot of a screen for determining the target position and the target orientation of the fixture. In the drawing, a reference numeral 390 denotes the neural tube, and a reference numeral 392 denotes the fixture.

Once the design is completed, the placement design data including the specifications, the target position, and the target orientation of the fixture are stored in the storage unit 110. Here, the information on the target position and the target orientation may be added to the 3D oral cavity image as a separate layer and constitute a part of the 3D oral cavity image after the design.

Surgery Guide

Figure 22:
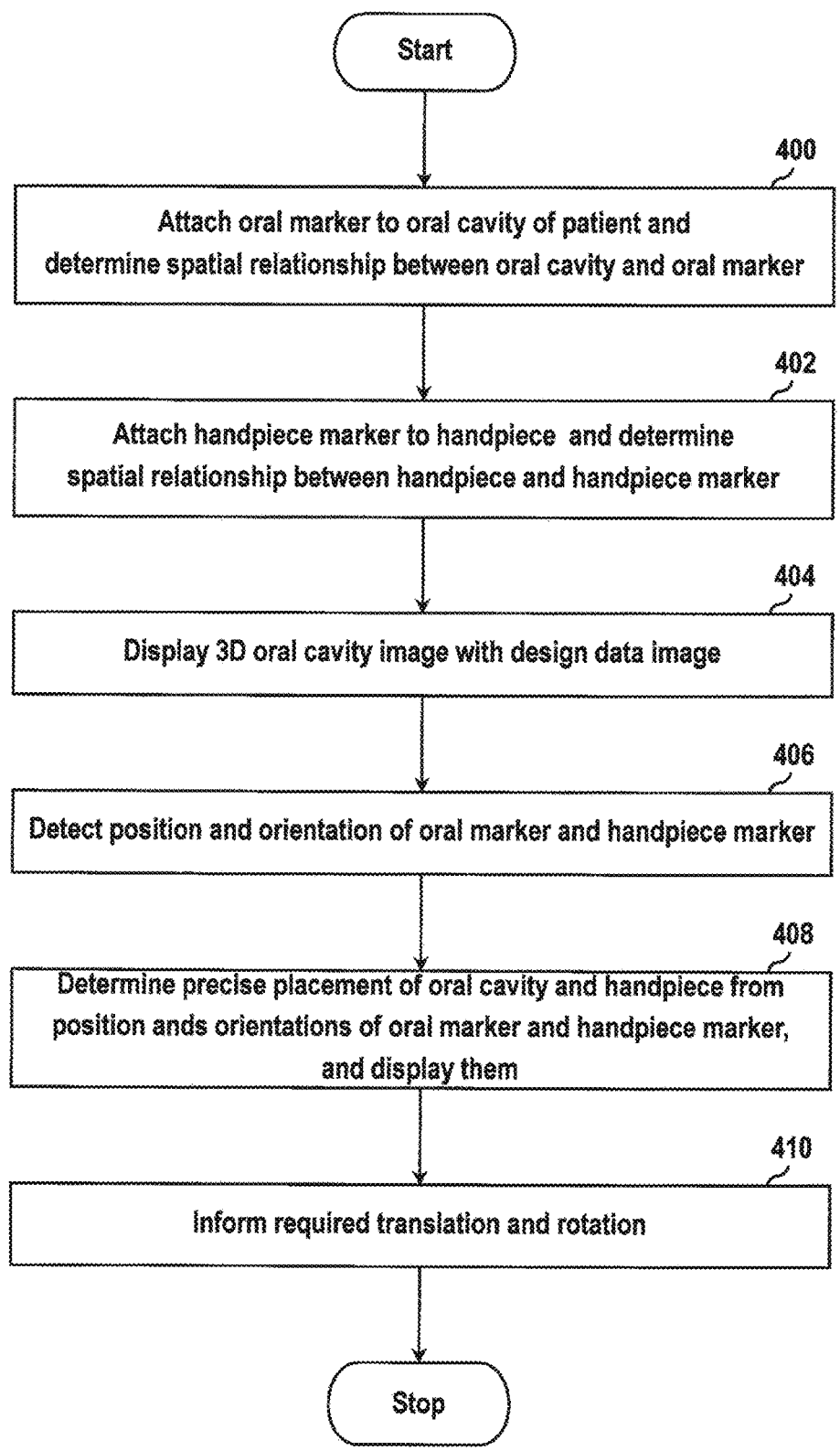
FIG. 22 is a flowchart illustrating an image guide process for an fixture implant surgery according to an exemplary embodiment of the present disclosure.

FIG. 22 illustrates the image guide process for the fixture implant surgery, in detail, according to an exemplary embodiment of the present disclosure.

First, in operation 400, an oral marker is attached to the jawbone, a neighboring structure such as teeth, or the face of the patient (hereinafter, referred to as "oral cavity"), and a spatial relationship between the jawbone or the oral cavity and the oral marker is determined. The term "spatial relationship" used herein refers to a relative position and a relative orientation which are parametric information that allows to know the position and orientation of one object when the position and orientation of the other object is known. In operation 402, a handpiece marker is attached to the handpiece used by the dentist, and the spatial relationship between the handpiece and the handpiece marker is determined.

Figure 23:
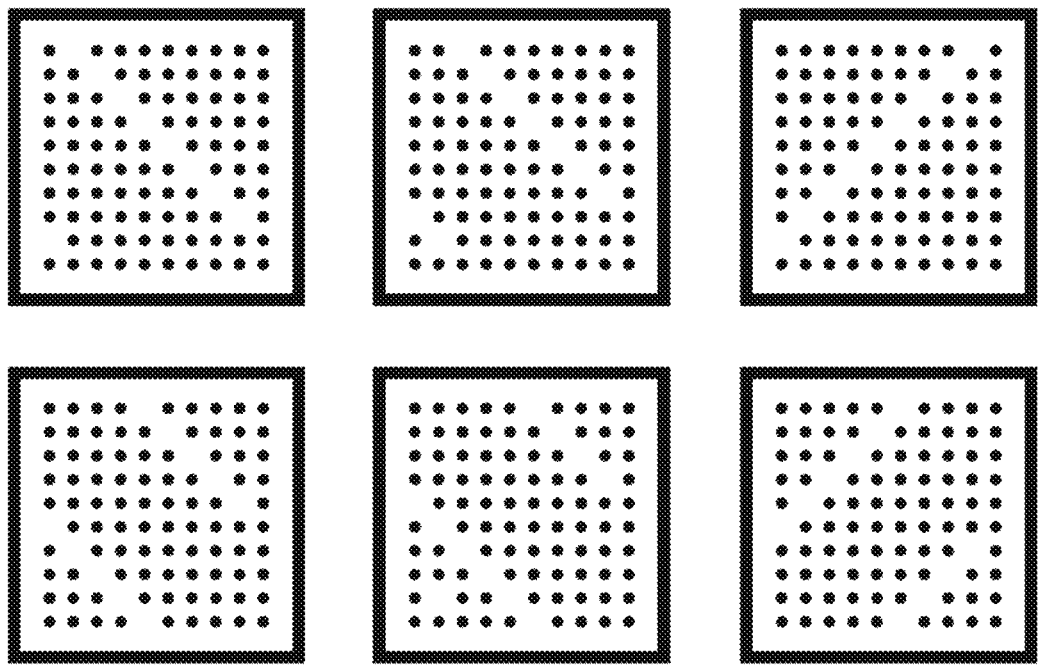
FIG. 23 illustrates examples of marker patterns used in an exemplary embodiment of the present disclosure.

FIG. 23 illustrates examples of marker patterns used in an exemplary embodiment of the present disclosure. In the present embodiment, all of the markers have a shape that a plurality of dots are arranged in a square frame. Each marker is different from other ones in the arrangement pattern of the dots. The oral marker, the handpiece marker, and a first and second auxiliary markers described below are chosen in advance among the plurality of markers shown in the drawing. In each of the markers, the center of the square may be defined as the origin of the marker. An x-axis may be defined to be a direction parallel to a certain edge and passing through the origin, an y-axis may be defined to be a direction to which the x-axis is rotated 90 degrees about the origin, and z-axis may be defined to be a direction emerging from the marker.

In attaching the markers to the oral cavity and the handpiece for use as the oral marker and the handpiece marker, it is important that the markers do not block the views of dentist and the hygienist. In view of this, each of the oral marker and the handpiece marker preferably is attached to the oral cavity and the handpiece using a separate tool.

Figure 24:
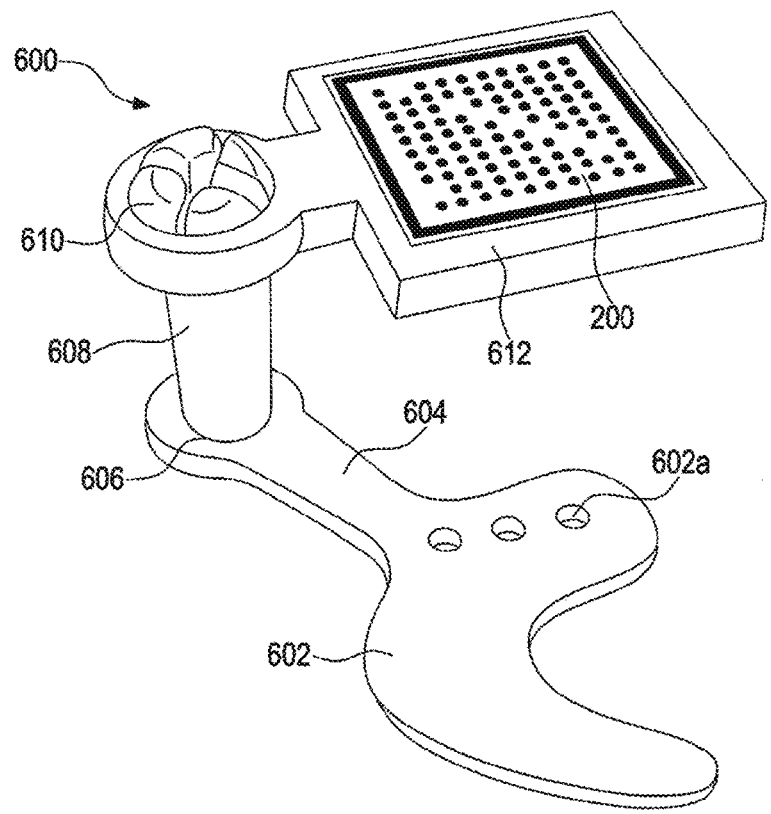
FIG. 24 illustrates an embodiment of an oral marker attachment tool for attaching an oral marker to an oral cavity.

FIG. 24 illustrates an embodiment of the oral marker attachment tool for attaching the oral marker to the oral cavity. In the illustrated embodiment, the oral marker attachment tool 600 includes a coupling portion 602, a protruding portion 604, a marker attaching panel 612, at least one ball joint 606 and 610, and one or more link arm 608. The coupling portion 602 may be attached to the patient's teeth. The protruding portion 604 may be partially exposed to the outside of the patient's lips when the tool is installed in the patient's teeth. On the marker attaching panel 612, attached is the oral marker 200. The at least one ball joint 606 and 610 and one or more link arm 608 connect the protruding portion 604 and the marker attaching panel 612. The coupling portion 602 may have a plurality of through holes 602a. The oral marker attachment tool 600 is preferably made of a plastic material so as to minimize its weight.

Figure 25:
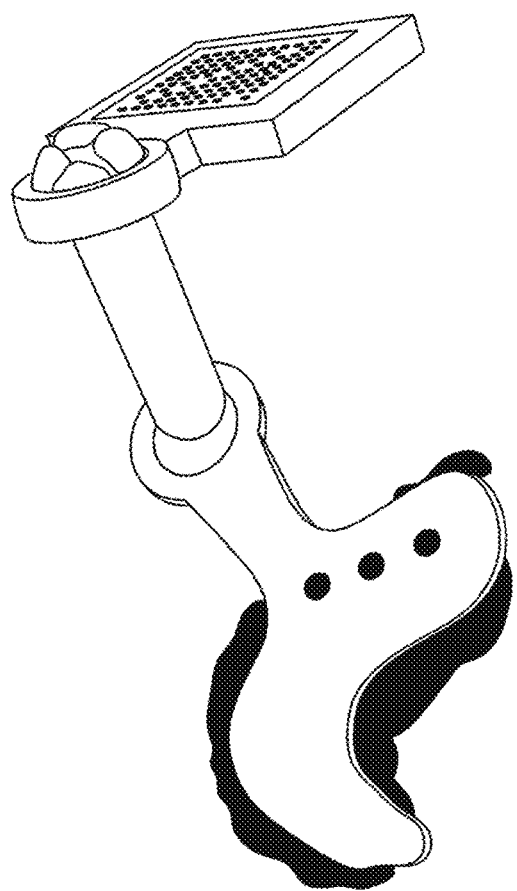
FIG. 25 illustrates an example of an oral marker attachment tool having an impression attached thereto.

The oral marker attachment tool 600 can be attached to the oral cavity by applying the impression material to a bottom surface of the coupling portion 602, placing the oral marker attachment tool 600 to be in close contact with teeth in the jawbone in which the surgery site is located (i.e. in the maxilla if the tooth site to be treated is in the maxilla, but in the mandible if the tooth site to be treated is in the mandible) but to be spaced apart from the surgery site, and waiting for a while until the impression material becomes elastically solid. After the impression material is cured, elastically solidified impression material is attached firmly to the coupling portion 602 so that the impression material does not fall off easily from the coupling portion 602. At this time, the impression material having penetrated into the plurality of through holes 602a formed in the coupling portion 602 increases the coupling force between the impression and the coupling portion 602. Meanwhile, the solidified impression material is also strongly attached to the teeth, so that the oral marker attachment tool 600 remains attached to the tooth via the impression material unless an external force is exerted intentionally to separate the oral marker attachment tool 600 from the tooth. Furthermore, the oral marker attachment tool 600 can be kept in close contact even when it is separated from the tooth and attached again to the tooth. On the other hand, even when the oral marker attachment tool 600 having the impression material attached thereto is separated from the tooth and attached to a corresponding portion on the oral gypsum model, the tool can maintain a state of close contact with the oral gypsum model. FIG. 25 illustrates an example of the oral marker attachment tool 600 having an impression attached thereto. Instead of directly attaching the oral marker attachment tool 600 to the patient's mouth immediately after the application of the impression material, it is possible to attach the oral marker attachment tool 600 preliminarily to the oral gypsum model and then transfer to the mouth after the impression material is cured.

After the oral marker attachment tool 600 with the impression is attached to the oral cavity, the arrangement of the oral marker attachment tool 600 may be adjusted to be in an optimum placement by using the ball joint 606 or 610 and the link arm 608, so that the oral marker attachment tool 600 does not interfere any work of the dentist or the hygienist work and does not hinder the operation of the system according to the present disclosure. Therefore, the oral marker 200 or the oral marker attachment tool 600 do not interfere with a view of the dentist, obstruct the approach or use of the handpiece, obstruct the movement of an inhaler of the hygienist. Also, the oral marker 200 is prevented from being pushed against the lips of the patient, but can be easily removed in an emergency. Further, the oral marker 200 can be easily seen even by the camera sensor 150.

Figure 26:
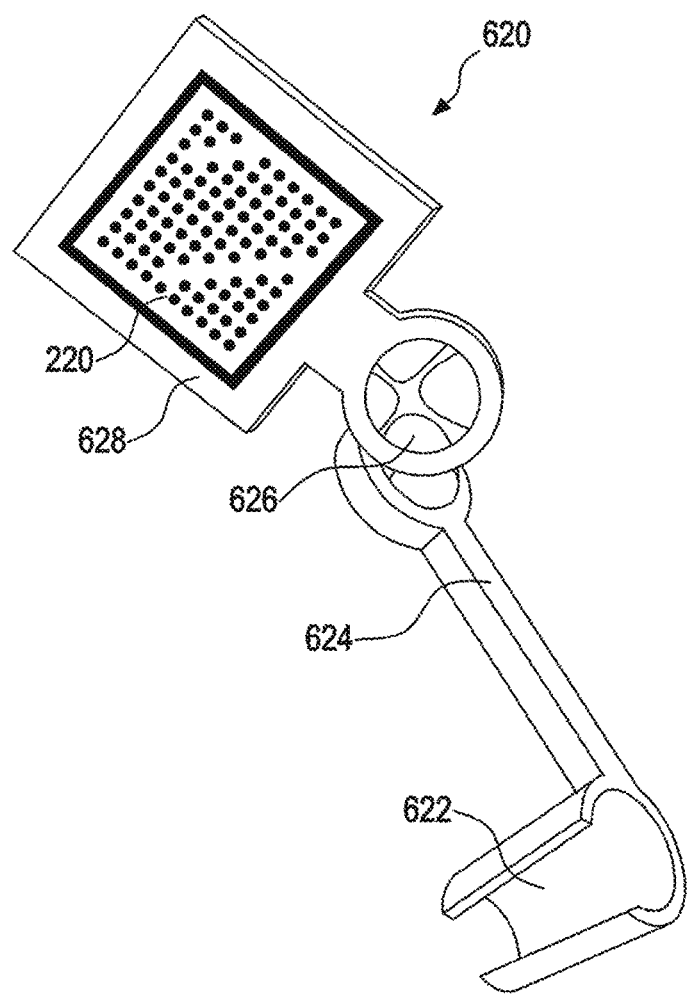
FIG. 26 illustrates an embodiment of a handpiece marker attachment tool for attaching a handpiece marker to a handpiece.
Figure 27:
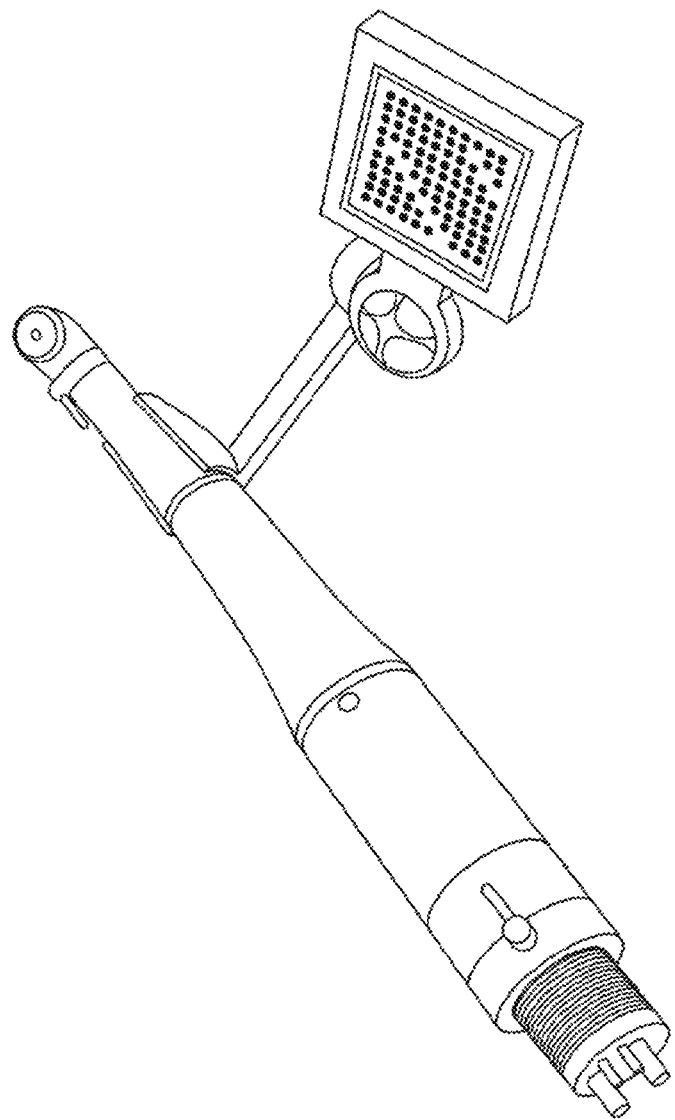
FIG. 27 illustrates a handpiece having the handpiece marker attached thereto via the handpiece marker attachment tool.

FIG. 26 illustrates an embodiment of a handpiece marker attachment tool for attaching the handpiece marker to the handpiece. In the illustrated embodiment, the handpiece marker attachment tool 620 includes a clip 622 for attaching to a side of the handpiece, a marker attachment panel 628 for attaching the handpiece marker 220, one or more link arms 624 and one or more ball joints 626 for connecting the marker attaching panel 628 to the clip 622. The handpiece marker attaching tool 620 is preferably made of a plastic material so as to minimize the weight. The oral marker attachment tool 600 can be easily attached to the handpiece by fitting the clip 622 on an outer surface of the handpiece. FIG. 27 illustrates the handpiece marker attached to handpiece via the handpiece marker attachment tool.

After the handpiece marker 220 is attached to the handpiece by the handpiece marker attachment tool 620, the arrangement of the handpiece marker attachment tool 620 may be adjusted to be in an optimum placement by using the link arm 624 and the ball joint 626, so that the handpiece marker attachment tool 620 does not interfere any work of the dentist or the hygienist work and does not hinder the operation of the system according to the present disclosure. Therefore, the handpiece marker 220 or the handpiece marker attachment tool 620 do not interfere with a view of the dentist, obstruct the approach or use of the handpiece, obstruct the movement of an inhaler of the hygienist. Also, the handpiece marker 220 is prevented from being pushed against the lips of the patient, but can be easily removed in an emergency. Further, the handpiece marker 220 can be easily seen even by the camera sensor 150.

After the installation of the oral marker 200 and the handpiece marker 220, it is possible to precisely trace the movement of the jawbone and the handpiece in real-time by tracking the oral marker 200 and the handpiece marker 220, respectively, and display the real-time placement of the jawbone and the hand piece on the screen.

Referring back to FIG. 22, in the tracking process, the 3D oral cavity image to which the placement design data is added is first displayed on the monitor 190 of the surgery guide PC 160 (operation 404).

After the surgery is initiated, the camera sensor 150 continuously detects the position and orientation of the oral marker 200 and the handpiece marker 220 to provide to the surgery guide PC 160 (operation 406). In one embodiment, the camera sensor 150 provides the surgery guide PC 160 with six kinds of data for each of the oral marker 200 and the handpiece marker 220, which data include three-dimensional positions (e.g., an x-axis coordinate, an y-axis coordinate, a z-axis coordinate) and the rotation angle with respect to the three-dimensional direction (e.g., rotation angles with respect to the x-, y-, and z-axes). The surgery guide program executed in the surgery guide PC 160 determines the precise position of the jawbone (i.e. the maxilla or the mandible on which the surgery is carried out) reflecting the motion of the jawbone by use of the position and orientation of the oral marker 200 (operation 408). Also, the surgery guide program determines the precise position of the handpiece reflecting the motion of the handpiece by use of the position and orientation of the t handpiece marker 220. The surgery guide program updates the display shown in the screen in real-time.

In addition to tracking the movements of the patient's oral cavity and the handpiece and displaying the oral cavity and the handpiece, the surgery guide program may provide the dentist with a required amount of translation and a required amount of rotation of the handpiece through the screen or through the screen and a headset speaker (operation 410).

On the other hand, the spatial relationships between the oral cavity and the oral marker and between the handpiece and the handpiece marker should be identified, as mentioned above with respect to operations 400 and 402 in FIG. 20, in order track the oral marker 200 and the handpiece marker 220 and estimate the position of the oral cavity and the handpiece.

Figure 28:
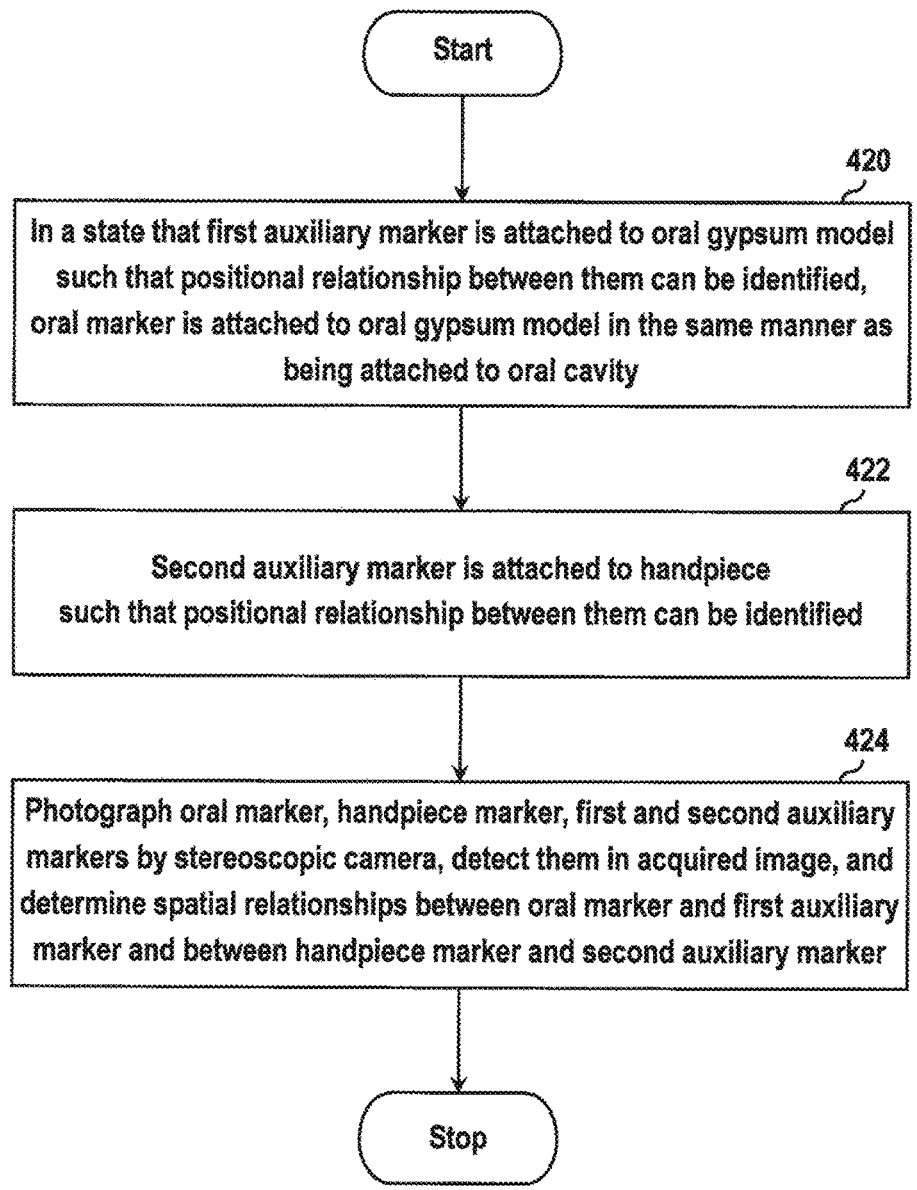
FIG. 28 is a flowchart illustrating a method of determining a spatial relationship between an oral cavity and the oral marker and a spatial relationship between the handpiece and the handpiece marker according to an exemplary embodiment of the present disclosure.

FIG. 28 illustrates a method of determining a spatial relationship between an oral cavity and the oral marker and a spatial relationship between the handpiece and the handpiece marker according to an exemplary embodiment of the present disclosure.

According to the illustrated embodiment, in a state that the first auxiliary marker is attached to the oral gypsum model in such a manner that a positional relationship between the first auxiliary marker and the oral gypsum model can be clearly identified, the oral marker is attached to the oral gypsum model in the same manner as it is attached to the oral cavity (operation 420).

Figure 29:
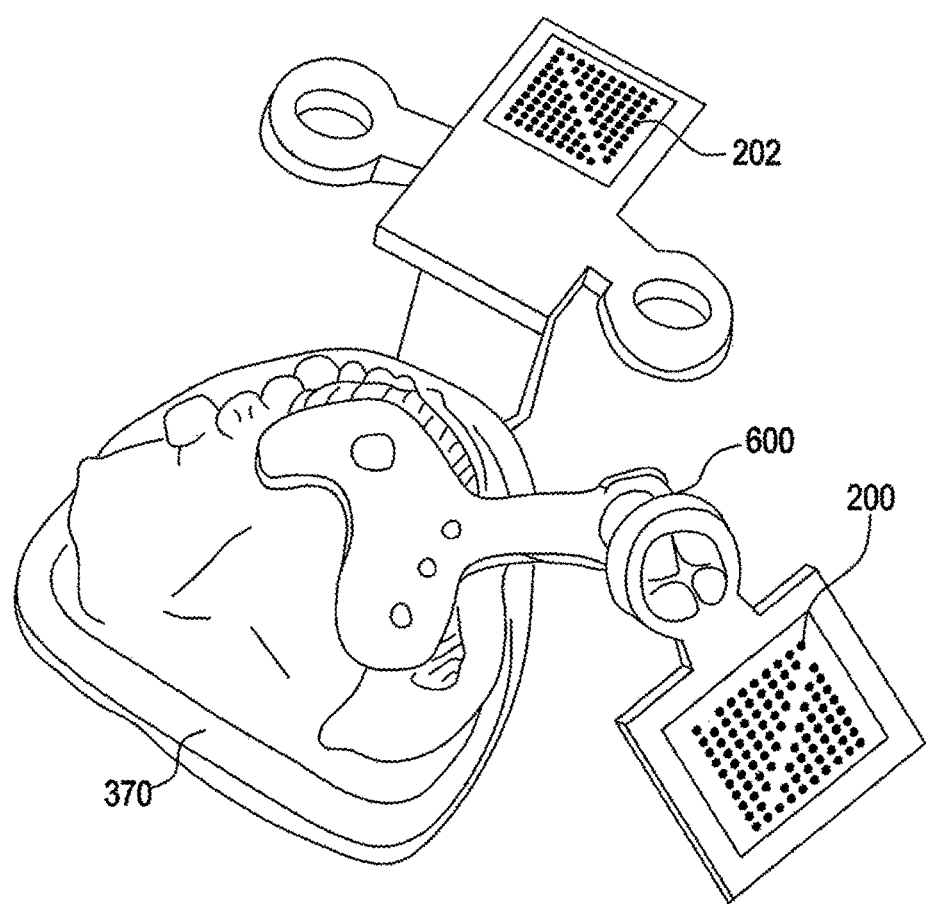
FIG. 29 illustrates a state that the oral gypsum model is placed on a cradle with a first auxiliary marker attached thereto and the oral marker is attached to the oral gypsum model via the oral marker attachment tool.
Figure 30:
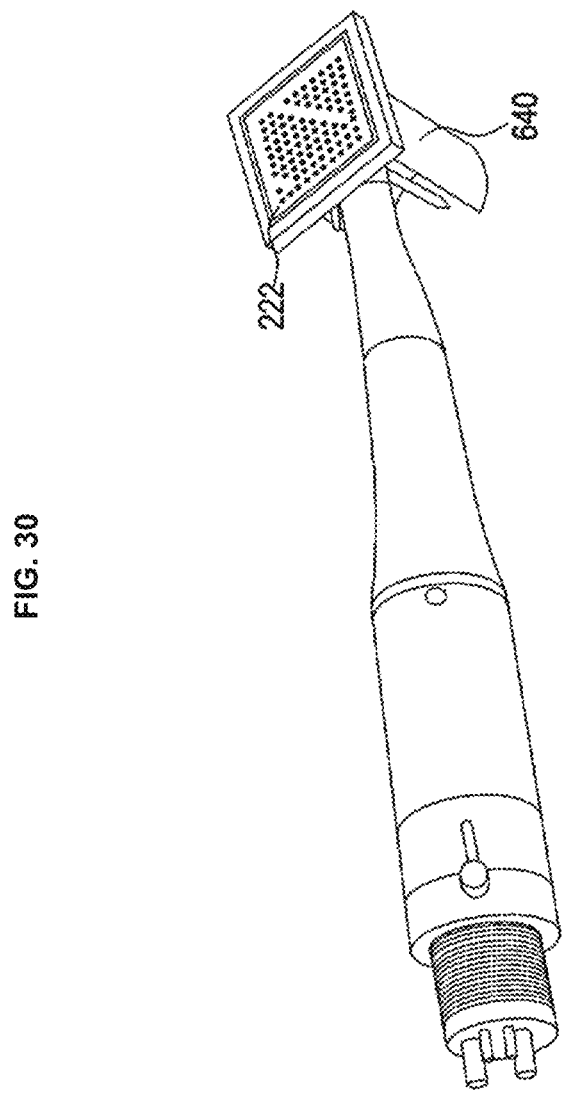
FIG. 30 illustrates an example a state that a second auxiliary marker is attached to the handpiece.

Here, the oral gypsum model on the cradle 370 described with reference to FIG. 12 may be utilized. It is easy to detect the exact position and shape of the oral gypsum model with respect to the cradle 370 from the third CT image acquired from the arrangement of FIG. 12 or the third vector image. Meanwhile, if the shape of each cradle is the same as each other and the first auxiliary marker 202 is attached uniformly at a certain position, the positional relationship between the cradle 370 and the first auxiliary marker 202 is unique and clear. Thus, the spatial relationship between the oral gypsum model and the first auxiliary marker 202 can be uniquely determined via the cradle 370 and can be identified clearly. In the arrangement of FIG. 12, the oral marker attachment tool 600 with the impression attached thereto is attached to the oral gypsum model to be in close contact with the model. FIG. 29 illustrates a state that the oral gypsum model is placed on the cradle 370 with a first auxiliary marker 202 attached thereto and the oral marker 200 is attached to the oral gypsum model via the oral marker attachment tool 600.

Figure 31:
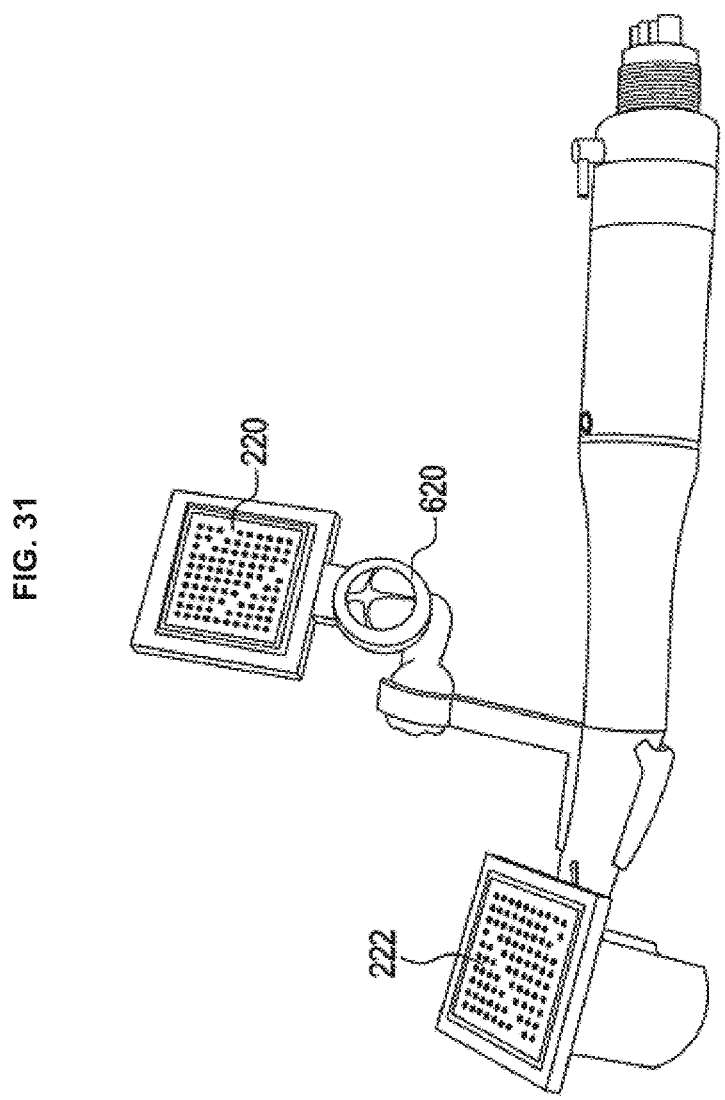
FIG. 31 illustrates an example of a state that the handpiece marker and the second auxiliary marker are attached to the handpiece.

Referring back to FIG. 28, the second auxiliary marker is attached to the handpiece in such a manner that a positional relationship between the second auxiliary marker and the handpiece can be clearly identified in operation 422. For example, the second auxiliary marker 222 can be attached to the upper surface of a handpiece head which meets a virtual extension line of a center axis of the drilling tool in the handpiece. In particular, an auxiliary marker attachment tool 640 to which the second auxiliary marker 222 is attached may be engaged temporarily with the handpiece head. In this state, the handpiece marker 220 may be attached to the handpiece by use of the handpiece marker attachment tool 620. FIG. 31 illustrates an example of a state that the handpiece marker 220 and the second auxiliary marker 222 are attached to the handpiece.

Referring back to FIG. 28, in operation 424, the oral marker 200, the handpiece marker 220, the first and second auxiliary markers 202 and 222 are photographed by a stereoscopic camera or two image sensors of the camera sensor 150, and they are detected in the acquired image. Also, the spatial relationships between the oral marker 200 and the first auxiliary marker 202 and between the handpiece marker 220 and the second auxiliary marker 222 are determined. In more detail, the camera sensor 150 discriminates each marker from other ones based on the dot patterns printed on the markers. Then, the camera sensor 150 three-dimensionally restores the dots in each marker, calculates the position and the orientation of the marker based with respect to a camera coordinate system, and outputs position data and orientation data for each marker to the surgery guide PC 160. The surgery guide PC 160 determines the spatial relationship between the oral marker 200 and the first auxiliary marker 202, i.e., a distance and a rotation angle. Also, surgery guide PC 160 determines a distance and a rotation angle between the handpiece marker 220 and the second auxiliary marker 222. Arithmetic operations for the spatial relationships between the markers may be carried out by the camera sensor 150 rather than the surgery guide PC 160.

Once the spatial relationship between the oral marker 200 and the first auxiliary marker 202 is determined, the spatial relationship between the oral cavity and the oral marker 200 can readily be determined since the spatial relationship between each point in the oral cavity and the first auxiliary marker 202 is identified already. For example, when each of the points in the oral cavity is described in terms of a coordinate system of the first auxiliary marker 202, the coordinate system can be converted into a coordinate system of the oral marker 200 using the spatial relationship between the oral marker 200 and the first auxiliary marker 202, and can be converted again as necessary so as to be rendered in a viewpoint of camera or another viewpoint while reflecting the motion of the jawbone.

Similarly, once the spatial relationship between the handpiece marker 220 and the second auxiliary marker 222 is determined, the spatial relationship between the handpiece and the handpiece marker 220 can readily be determined since the spatial relationship between the handpiece and the second auxiliary marker 222 is identified already. For example, when each of the points on the handpiece is described in terms of a coordinate system of the second auxiliary marker 222, the coordinate system can be converted into a coordinate system of the handpiece marker 220 using the spatial relationship between handpiece marker 220 and second auxiliary marker 222, and can be converted again as necessary so as to be rendered in a viewpoint of camera or another viewpoint while reflecting the motion of the handpiece.

Figure 32:
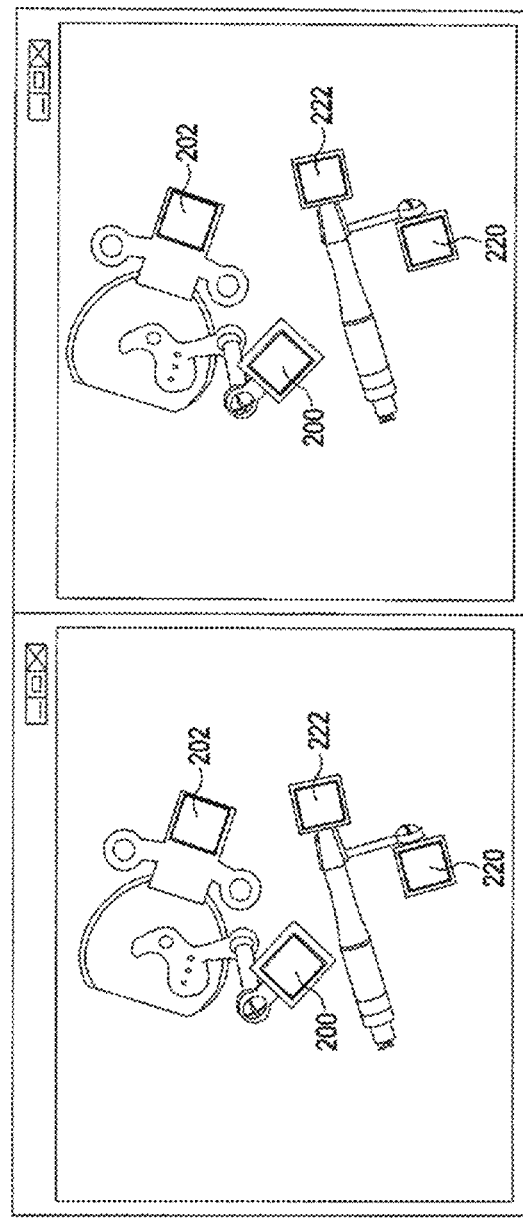
FIG. 32 illustrates exemplary images taken by the camera sensor 150 and displayed on a screen and the markers in the images during a marker registration process just before the implant surgery.

The operations 420-424 of FIG. 28, which may be understood as a marker position matching procedure or a marker registration procedure, can be carried out simply immediately before the implant surgery for the patient. FIG. 32 illustrates exemplary images taken by the camera sensor 150 and displayed on a screen and the markers in the images during a marker registration process just before the implant surgery. In the drawings, a left image is the image acquired by the first image sensor, and the right image is the image acquired by the second image sensor. As described above, the orientations of the first auxiliary marker 202, the oral marker 200, the second auxiliary marker 222, and the handpiece marker 220, and the spatial relationships between the first auxiliary marker 202 and the oral marker 200 and between the second auxiliary marker 222 and the handpiece marker 220 can be detected from these images.

While only the spatial relationship between two markers to be matched may be detected during a marker registration phase in an embodiment, and the coordinate systems for describing the oral cavity or the handpiece may be converted to another coordinate system in another embodiment al changed. Depending on a scope of the operations carried out during the marker registration phase, operations of positioning and rendering objects based on the detection of markers may be changed slightly during the tracking of the jawbone and the handpiece.

FIG. 33 illustrates a jawbone positioning and rendering process during the implant surgery in an embodiment where only the spatial relationship (i.e. a distance, and a difference in direction or an angle to be rotated) between the first auxiliary marker 202 and the oral marker 200 is recorded during a marker registration. In this case, if the position of the oral marker 200 is determined during the surgery (operation 440), a vector operation corresponding to a process of determining the virtual position of the second auxiliary marker 202 corresponding to the position of the oral marker 200 is performed (operation 442). Then, the position of the jawbone corresponding to the virtual position of the first auxiliary marker 202 is determined and the jawbone is rendered (operation 444).

FIG. 34 illustrates the jawbone positioning and rendering process during the implant surgery in another embodiment where the coordinates of the jawbone and other oral structures described in a coordinate system of the first auxiliary marker 202 are described again according to a coordinate system of the oral marker 200 during the marker registration. In this case, if the position of the oral marker 200 is determined during the surgery (operation 460), the position of the jawbone corresponding to the position of the first auxiliary marker 202 is readily determined utilizing the re-described positional information of the jawbone and the jawbone is rendered (operation 462).

Figure 35:
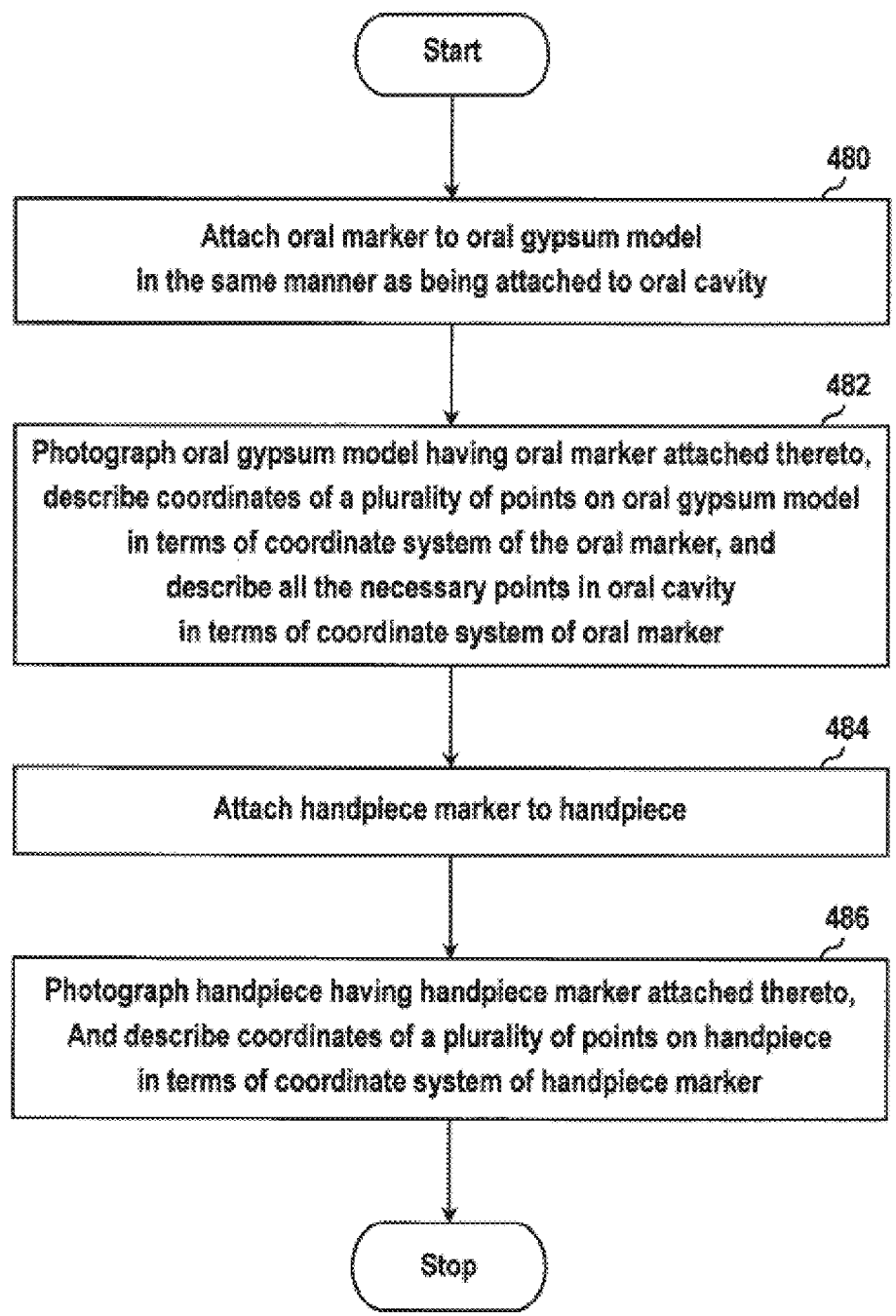
FIG. 35 is a flowchart illustrating the method of determining the spatial relationship between the oral cavity and the oral marker and the spatial relationship between the handpiece and the handpiece marker according to another exemplary embodiment of the present disclosure, which is an alternative of the method shown in FIG. 28.

FIG. 35 illustrates the method of determining the spatial relationship between the oral cavity and the oral marker and the spatial relationship between the handpiece and the handpiece marker according to another exemplary embodiment of the present disclosure, which is an alternative of the method shown in FIG. 28.

According to this embodiment, the oral marker 200 is attached to the oral gypsum model in the same manner as it is attached to the oral cavity (operation 4800). In other words, the oral marker attachment tool 600 with the impression attached thereto is adhered to the oral gypsum model, in particular, at the position corresponding to the attachment position in the oral cavity.

Subsequently, the oral gypsum model and the oral marker 200 attached to the oral gypsum model is photographed with the stereoscopic camera of the camera sensor 150 or two image sensors. Then, the coordinates of a plurality of points on the oral gypsum model are described in terms of the coordinate system of the oral marker 200. Further, the coordinates of all the points may be described in terms of the coordinate system of the oral marker 200 using the corresponding relationship between the oral gypsum model and oral cavity (operation 482).

Next, the handpiece marker is attached to the handpiece using the handpiece marker attachment tool 620 shown in FIG. 24 (operation 484).

Then, the handpiece with the handpiece marker 220 attached thereto is photographed with a stereoscopic camera or two image sensors of the camera sensor 150, and the coordinates of a plurality of points on the handpiece are described in terms of the coordinate system of the handpiece marker 220 (operation 486).

The output image for the surgery image guide of the surgery guide program 170 can be in various forms.

For example, a screen may be divided into a plurality of viewports, so that each viewport may be used to display a perspective view, a front view, a top view, or a side view, for example. Alternatively, only a perspective view may be displayed in a single viewport. When only a single view is displayed in the single viewport, the viewport may rendered in a viewpoint the camera. Also, the viewport may be detected and changed automatically by the program, or may be set to the viewpoint of the dentist.

The enlargement magnification of the image may be dynamically varied according to the operation progress or a moving range of the handpiece. Alternatively, a fixed magnification may be maintained. Also, in the rendering of the handpiece, the entire handpiece may be rendered, but only the drilling tool portion may be rendered for a simpler user interface.

The reference information to be added may also be changed according to the screen setting and the user input. For example, a required translation amount and translation direction of the handpiece may be displayed along with a required rotation amount and rotation direction of the handpiece. In addition, a depth of drilling or a remaining depth may be displayed during drilling. A warning beep or a guidance sound may be output if necessary, but such a sound information may be output preferably only to an earphone, a headphone, or a headset so as not to cause any anxiety of the patient.

Figure 36:
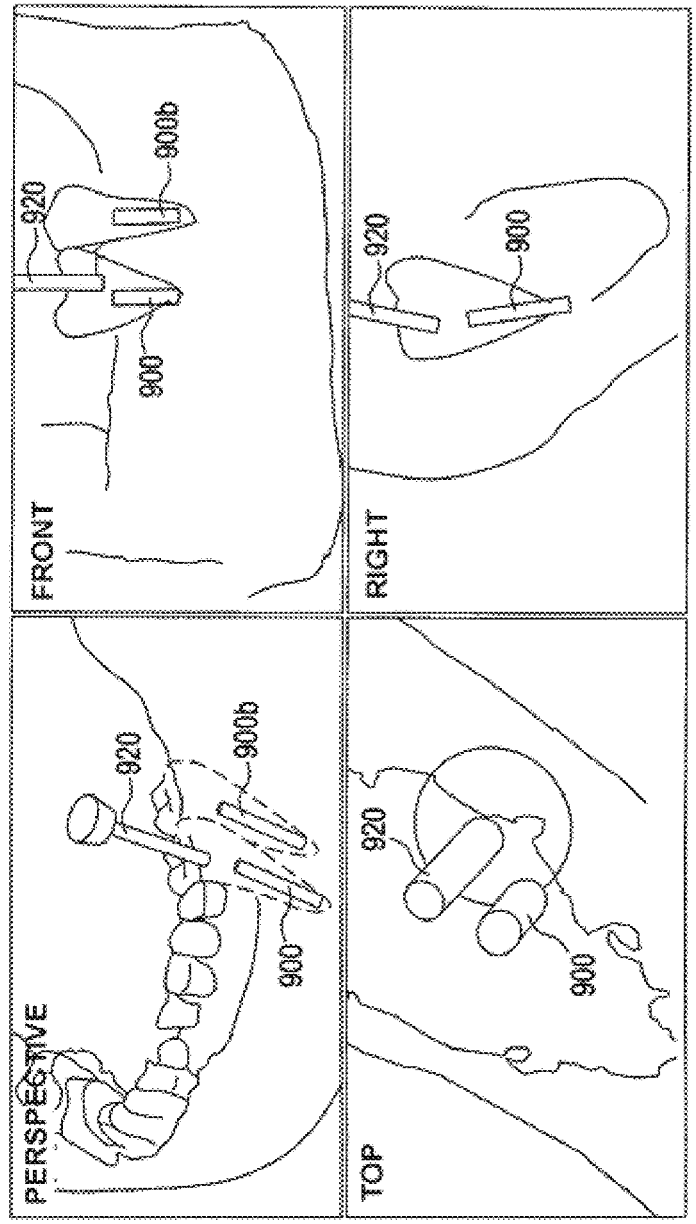
FIG. 36 is an exemplary output image of a surgery image guide according to an exemplary embodiment of the present disclosure.

FIG. 36 shows an example of the output image. In this output image, the screen is divided into four viewports, and each viewport displays a perspective view, a front view, top view, and a side view. An enlarged view centered on the fixture 900 or 900b in the design and the handpiece 920 can be displayed in each viewport. For a simpler user interface, only a front end portion or the drilling tool portion may be rendered for the handpiece 920.

Figure 37:
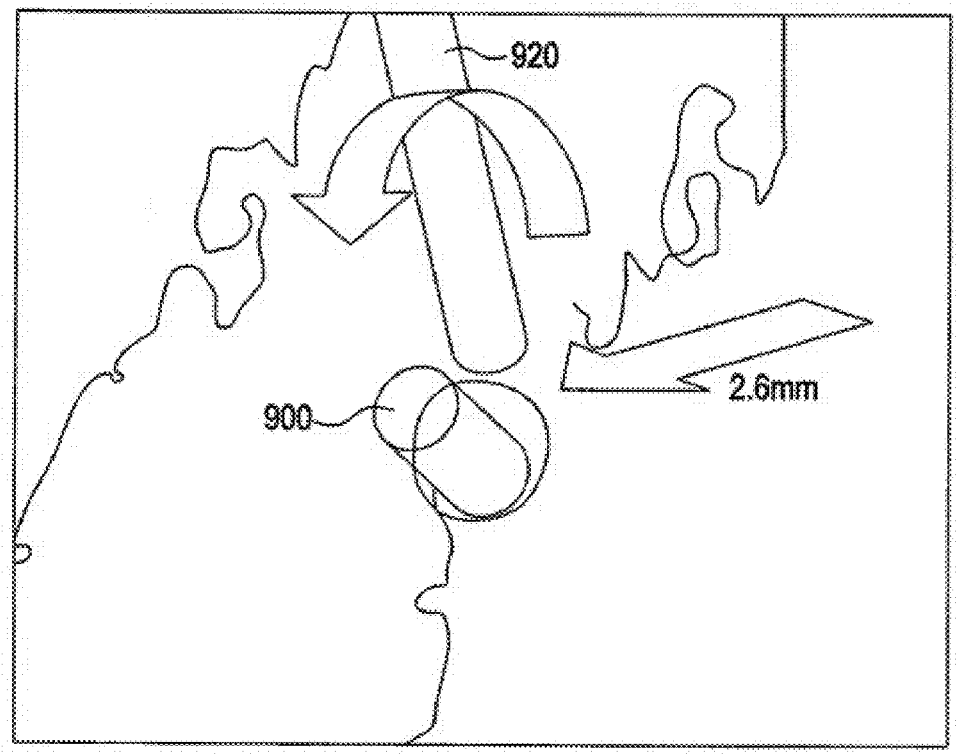
FIG. 37 is an exemplary output image of the surgery image guide according to another exemplary embodiment of the present disclosure.

FIG. 37 shows another example of the output image. This output image includes only a single viewport, and a perspective view in a viewpoint of the camera or the dentist may be displayed in this viewpoint. The fixture 900 in the design and the handpiece 920 can be displayed centrally. The required translation amount and translation direction, and a required rotation amount and rotation direction of the handpiece may be displayed additionally.

While the present disclosure has been particularly shown and described with reference to exemplary embodiments thereof, it is to be understood that the present disclosure is not limited to the disclosed embodiments, but may be modified in various manners or embodied in different implementations.

For example, though the embodiments where the camera sensor 150 includes two image sensors were described above, the present disclosure is not limited thereto and the camera sensor may include only a single image sensor.

The design program 130 executed on the design the PC 120 may be a combination of several programs rather than a single program. Also, some operations may be performed by an existing commercial program. For example, the operation of merging the first through third vector images may be performed using an existing image processing program having the merging function, for example, the DAVID program provided by David Vision System GmbH, Germany. Also, the conversion of the DICOM format into the STL format may be performed by a program commonly used for CT image processing.

Therefore, it should be understood that the above-described embodiments are illustrative in all aspects and not restrictive. Thus, it will be understood by those of ordinary skill in the art that various changes in form and details may be made therein without departing from the spirit and scope as defined by the following claims.

The invention claimed is:

1. An implant surgery guiding method, comprising:
   (a) generating a 3D oral cavity image of a patient by combining a CT image of an oral cavity including a jawbone of the patient and a gypsum model image of an oral gypsum model placed on a cradle having a predetermined shape and size;
   (b) designing a target placement including a target position and a target orientation of a fixture based on the 3D oral cavity image;
   (c) placing the oral gypsum model on the cradle attached with a first auxiliary marker at a predetermined position, attaching an oral marker that is to be attached to the jawbone of the patient on the oral gypsum model, taking a photograph of the oral gypsum model attached with the first auxiliary marker and the oral marker, and determining a spatial relationship between the oral marker and the jawbone in the 3D oral cavity image by using a spatial relationship between the oral marker and the first auxiliary marker, a spatial relationship between the first auxiliary marker and the cradle, and a spatial relationship between the cradle and the jawbone in the 3D oral cavity image;
   (d) attaching the oral marker to the jawbone of the patient, determining the spatial relationship between the oral marker and the jawbone in the 3D oral cavity image as the spatial relationship between the oral marker and the jawbone, attaching a handpiece marker on a handpiece of a dentist, and determining a spatial relationship between the handpiece marker and the handpiece; and
   (e) estimating positions and orientations of the jawbone and the handpiece based on changes in positions and orientations of the oral marker and the handpiece marker while tracking the motions of the oral marker and the handpiece marker, and displaying a jawbone image portion and a handpiece image portion on a screen reflecting real-time changes in the positions and orientations of the jawbone and the handpiece.

2. The implant surgery guiding method of claim 1, wherein the operation (a) comprises:
   applying an impression material to an impression assistant tool which may be partially exposed out of the oral cavity, taking an impression by making the patient bite the impression material, and acquiring the CT image of the oral cavity as a first base image while the impression is being taken;
   acquiring a second base image of the impression assistant tool to which the impression cured and separated from the oral cavity is attached;
   acquiring the gypsum model image of the oral gypsum model placed on the cradle as a third base image; and
   combining the first through the third base images to generate the 3D oral cavity image.

3. The implant surgery guiding method of claim 2, wherein the operation (a) comprises:

converting the first through the third base images to a first through a third vector images, respectively; and combining the first through the third vector images to generate the 3D oral cavity image.

4. The implant surgery guiding method of claim 3, wherein, when the first through the third vector images are combined to generate the 3D oral cavity image, the first and the second vector images are combined using a respective portion corresponding to the impression assistant tool in the first and second vector images, and the second and the third vector images are combined using surface shape information in a teeth portion.

5. The implant surgery guiding method of claim 3, wherein combining the first through the third base images comprises:

converting a negative imprint portion of teeth in the second vector image into a positive imprint portion; and combining the positive imprint portion of teeth in the second vector image with the corresponding teeth portion in the third vector image.

6. The implant surgery guiding method of claim 1, wherein the operation (b) comprises:

disposing teeth elements according to a predetermined standard teeth model in the 3D oral cavity image and adjusting a teeth arrangement;

disposing a standard tooth conforming to the standard teeth model at a tooth missing location where a placement of the fixture is required; and determining the target placement of the fixture such that the fixture does not interfere with a neural tube and is not exposed out of the jawbone.

7. The implant surgery guiding method of claim 6, wherein the determining the target placement of the fixture comprises:

determining a type of the fixture; and adding design data associated with the target placement of the fixture to the 3D oral cavity image as a part of the 3D oral cavity image.

8. The implant surgery guiding method of claim 1, wherein the operation (d) comprises:

attaching the oral marker to an oral cavity of the patient by using an oral marker attachment tool having one or more link arms; and attaching the handpiece marker to the handpiece by using a handpiece marker attachment tool having one or more link arms.

9. The implant surgery guiding method of claim 1, wherein a portion of the oral gypsum model where the oral marker is attached in the operation (c) corresponds to a location of the jawbone of the patient where the oral marker is attached in the operation (d).

10. The implant surgery guiding method of claim 1, wherein the operation (e) comprises:

detecting the position and the orientation of the oral marker; and determining the position and the orientation of the jawbone from the position and the orientation of the oral marker based on the spatial relationship between the first auxiliary marker and the oral marker.

11. The implant surgery guiding method of claim 1, wherein, in the operation (e), the 3D oral cavity image is rendered at a viewpoint of a camera or a dentist.

12. The implant surgery guiding method of claim 1, wherein, in the operation (e), a required translation amount and translation direction, and a required rotation amount and rotation direction of the handpiece are displayed additionally on the screen.

13. The implant surgery guiding method of claim 12, wherein a depth of drilling or a remaining depth is displayed additionally on the screen.

14. The implant surgery guiding method of claim 1, wherein the operation (d) comprises:

describing spatial arrangements of at least one of the jawbone and the oral marker and at least one of the handpiece and the handpiece marker in universal coordinates.

* * * * *